US011751760B2

(12) United States Patent
Inglese et al.

(10) Patent No.: US 11,751,760 B2
(45) Date of Patent: Sep. 12, 2023

(54) DENTAL IMAGING WITH PHOTON-COUNTING DETECTOR

(71) Applicant: Carestream Health, Inc., Rochester, NY (US)

(72) Inventors: Jean-Marc Inglese, Bussy Saint Georges (FR); Sylvie Bothorel, Paris (FR); Vincent Loustauneau, Fontenay sous Bois (FR); Donna Rankin-Parobek, Honeoye Falls, NY (US)

( * ) Notice: Subject to any disclaimer, the term of this patent is extended or adjusted under 35 U.S.C. 154(b) by 0 days.

(21) Appl. No.: 15/655,109

(22) Filed: Jul. 20, 2017

(65) Prior Publication Data

US 2017/0311910 A1 Nov. 2, 2017

Related U.S. Application Data

(63) Continuation of application No. 14/366,696, filed as application No. PCT/US2012/043510 on Jun. 21, 2012, now Pat. No. 9,743,893.

(30) Foreign Application Priority Data

Dec. 21, 2011 (WO) ........................ PCT/US11/66432

(51) Int. Cl.
*A61B 6/14* (2006.01)
*A61B 1/24* (2006.01)
(Continued)

(52) U.S. Cl.
CPC ................ *A61B 1/24* (2013.01); *A61B 6/025* (2013.01); *A61B 6/027* (2013.01); *A61B 6/032* (2013.01);
(Continued)

(58) Field of Classification Search
CPC ....................................................... A61B 6/14
See application file for complete search history.

(56) References Cited

U.S. PATENT DOCUMENTS 5,224,140 A * 6/1993 Virta ........................ A61B 6/14
378/38
5,263,494 A 11/1993 Margelos et al.
(Continued)

FOREIGN PATENT DOCUMENTS

EP 0 534 548 A1 9/1992
JP H07-275239 10/1995
(Continued)

OTHER PUBLICATIONS

International Search Report, Completed Jun. 21, 2012 for International Application No. PCT/US11/66432, 2 pages.
(Continued)

*Primary Examiner* — Thomas R Artman

(57) ABSTRACT

An extra-oral dental imaging apparatus for obtaining an image from a patient has a radiation source; a first digital imaging sensor that provides, for each of a plurality of image pixels, at least a first digital value according to a count of received photons that exceed at least a first energy threshold; a mount that supports the radiation source and the first digital imaging sensor on opposite sides of the patient's head; a computer in signal communication with the digital imaging sensor for acquiring a first two-dimensional image from the first digital imaging sensor; and a second digital imaging sensor that is alternately switched into place by the mount and that provides image data according to received radiation.

20 Claims, 34 Drawing Sheets

(51) Int. Cl.
 *A61B 6/02* (2006.01)
 *A61B 6/03* (2006.01)
 *A61B 6/00* (2006.01)
 *H04N 5/232* (2006.01)
 *H04N 5/32* (2023.01)
 *A61B 6/04* (2006.01)

(52) U.S. Cl.
 CPC ............... *A61B 6/14* (2013.01); *A61B 6/145* (2013.01); *A61B 6/4233* (2013.01); *A61B 6/4241* (2013.01); *A61B 6/4266* (2013.01); *A61B 6/4441* (2013.01); *A61B 6/4452* (2013.01); *A61B 6/482* (2013.01); *A61B 6/501* (2013.01); *A61B 6/5235* (2013.01); *H04N 5/23238* (2013.01); *H04N 5/32* (2013.01); *A61B 6/0421* (2013.01); *A61B 6/4085* (2013.01); *A61B 6/4458* (2013.01); *A61B 6/54* (2013.01); *A61B 6/588* (2013.01)

(56) References Cited

U.S. PATENT DOCUMENTS

| | | | |
|---|---|---|---|
| 5,677,940 A | 10/1997 | Suzuki et al. | |
| 6,052,428 A | 4/2000 | Nakano et al. | |
| 6,118,842 A | 9/2000 | Arai et al. | |
| 6,466,641 B1* | 10/2002 | Virta | A61B 6/14 378/38 |
| 7,197,109 B2* | 3/2007 | Rotondo | A61B 6/14 378/196 |
| 7,397,890 B2* | 7/2008 | Sukovic | A61B 6/032 378/38 |
| 7,424,091 B2* | 9/2008 | Park | A61B 6/14 378/39 |
| 7,577,232 B2* | 8/2009 | Tachibana | A61B 6/14 378/116 |
| 7,646,845 B2 | 1/2010 | Lecomte et al. | |
| 7,672,425 B2* | 3/2010 | Rotondo | A61B 6/14 378/196 |
| 7,780,350 B2 | 8/2010 | Tranchant et al. | |
| 7,945,016 B2* | 5/2011 | Bothorel | A61B 6/14 378/148 |
| 7,961,841 B2* | 6/2011 | Ro | A61B 6/4429 378/116 |
| 8,005,186 B2* | 8/2011 | Lee | A61B 6/032 378/13 |
| 8,503,604 B2* | 8/2013 | Inglese | A61B 6/14 378/19 |
| 9,743,893 B2* | 8/2017 | Inglese | A61B 6/14 |
| 2002/0034277 A1 | 3/2002 | Laner | |
| 2004/0190678 A1* | 9/2004 | Rotondo | A61B 6/14 378/38 |
| 2005/0139757 A1* | 6/2005 | Iwanczyk | G01T 1/2928 250/239 |
| 2006/0239400 A1* | 10/2006 | Sukovic | A61B 6/032 378/38 |
| 2006/0256921 A1* | 11/2006 | Tachibana | A61B 6/14 378/116 |
| 2007/0030951 A1* | 2/2007 | Park | A61B 6/14 378/38 |
| 2007/0297564 A1* | 12/2007 | Rotondo | A61B 6/14 378/39 |
| 2008/0267343 A1* | 10/2008 | Sukovic | A61B 6/032 378/4 |
| 2008/0298554 A1 | 12/2008 | Tacconi et al. | |
| 2008/0317200 A1 | 12/2008 | Lecomte et al. | |
| 2009/0124882 A1 | 5/2009 | Massie et al. | |
| 2009/0245461 A1* | 10/2009 | Lee | A61B 6/032 378/38 |
| 2010/0034340 A1 | 2/2010 | Spartiotis et al. | |
| 2010/0074402 A1* | 3/2010 | Bothorel | A61B 6/14 378/38 |
| 2010/0074403 A1* | 3/2010 | Inglese | A61B 6/14 378/39 |
| 2010/0128840 A1* | 5/2010 | Cha | A61B 6/14 378/4 |
| 2010/0172462 A1 | 7/2010 | Tancredi et al. | |
| 2010/0195786 A1* | 8/2010 | Ro | A61B 6/4411 378/4 |
| 2010/0278299 A1 | 11/2010 | Loustauneau et al. | |
| 2010/0303204 A1 | 12/2010 | Erhardt et al. | |
| 2011/0044520 A1* | 2/2011 | Nakai | A61B 6/032 382/131 |
| 2012/0039436 A1 | 2/2012 | Bothorel et al. | |
| 2013/0307923 A1 | 11/2013 | Inglese et al. | |
| 2015/0004558 A1* | 1/2015 | Inglese | A61B 6/14 433/29 |
| 2017/0311910 A1* | 11/2017 | Inglese | A61B 6/032 |

FOREIGN PATENT DOCUMENTS

| | | |
|---|---|---|
| JP | 2847655 B | 1/1999 |
| JP | 2006-187607 A | 7/2006 |
| JP | 2008-092990 | 4/2008 |
| JP | 2008-229322 | 10/2008 |
| JP | 2009-502227 A | 1/2009 |
| JP | 2011-085479 | 4/2011 |
| JP | 2013-524859 | 6/2013 |
| WO | 2010/128404 A1 | 11/2010 |
| WO | 2011/013771 A1 | 2/2011 |
| WO | WO 2012/086648 A | 6/2012 |
| WO | 2012/168756 A1 | 12/2012 |

OTHER PUBLICATIONS

International Search Report, Complete Feb. 1, 2013 for International Application No. PCT/US12/43510, 2 pages.
Supplementary European Search Report, Application No. EP12859406, dated Jun. 18, 2015, 2 pages.

* cited by examiner

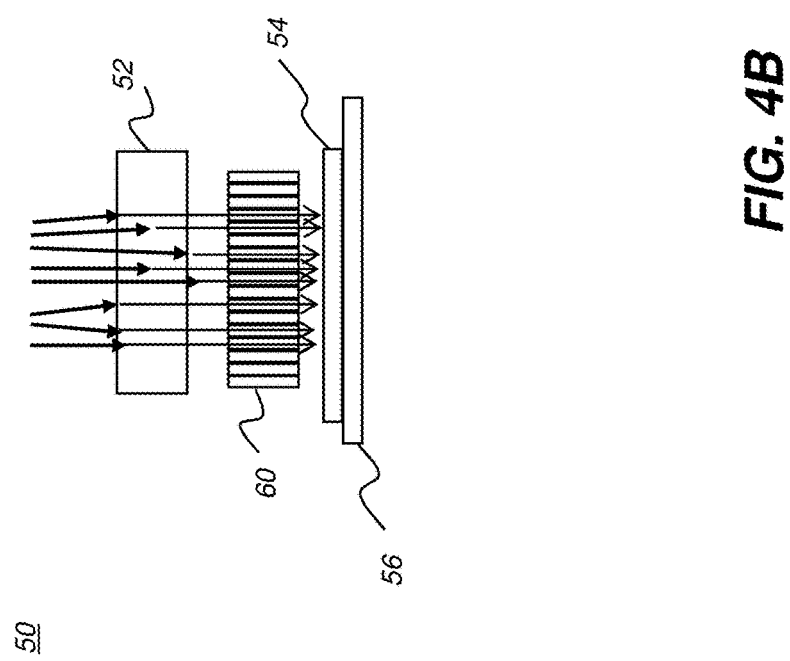

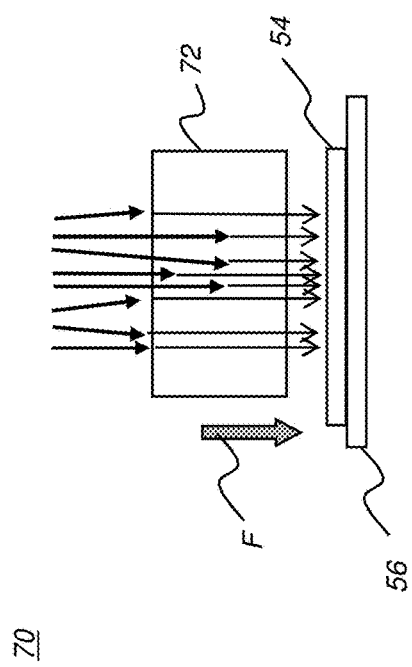

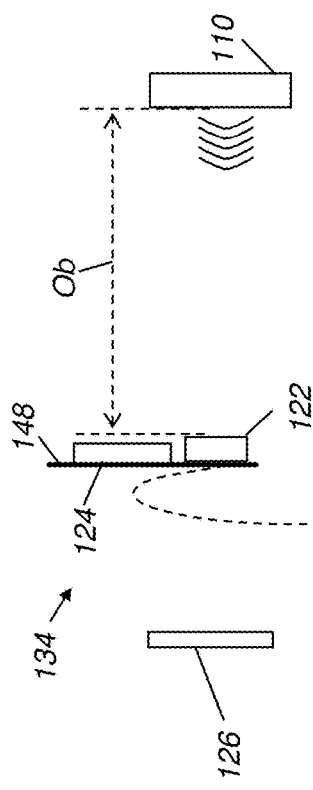
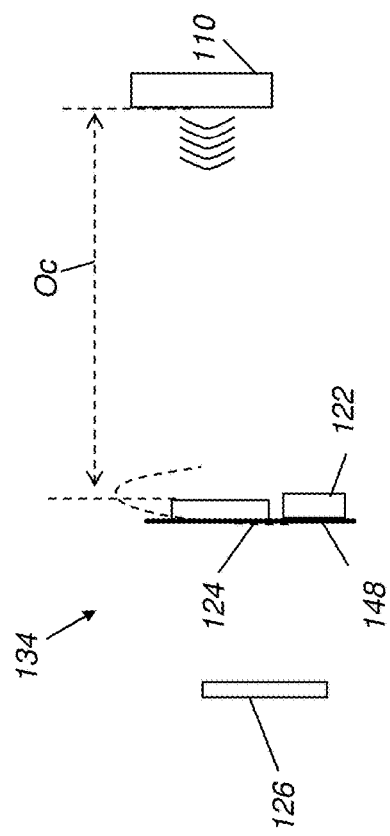

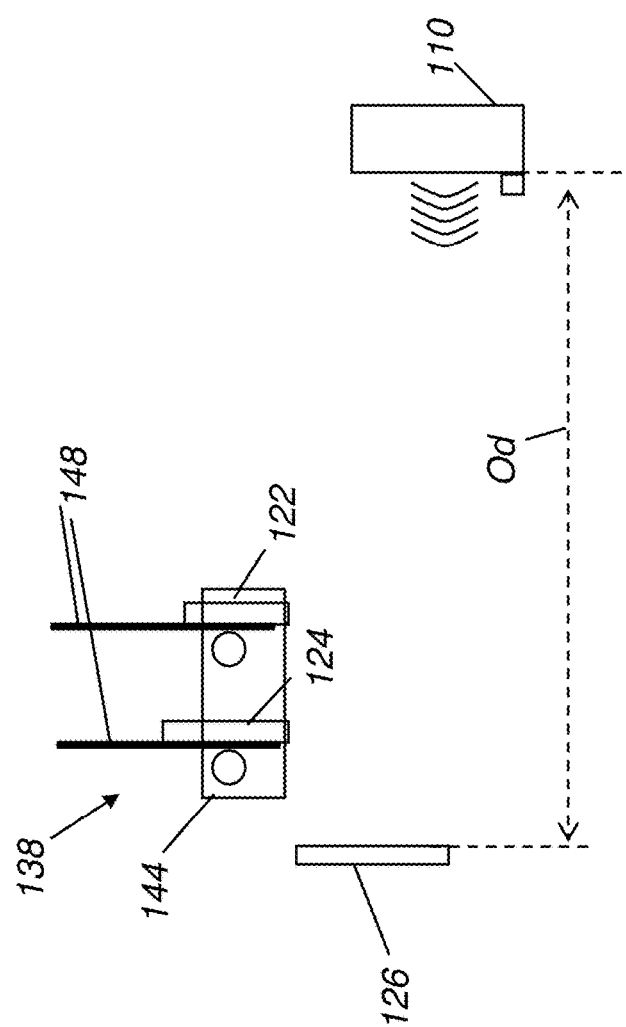

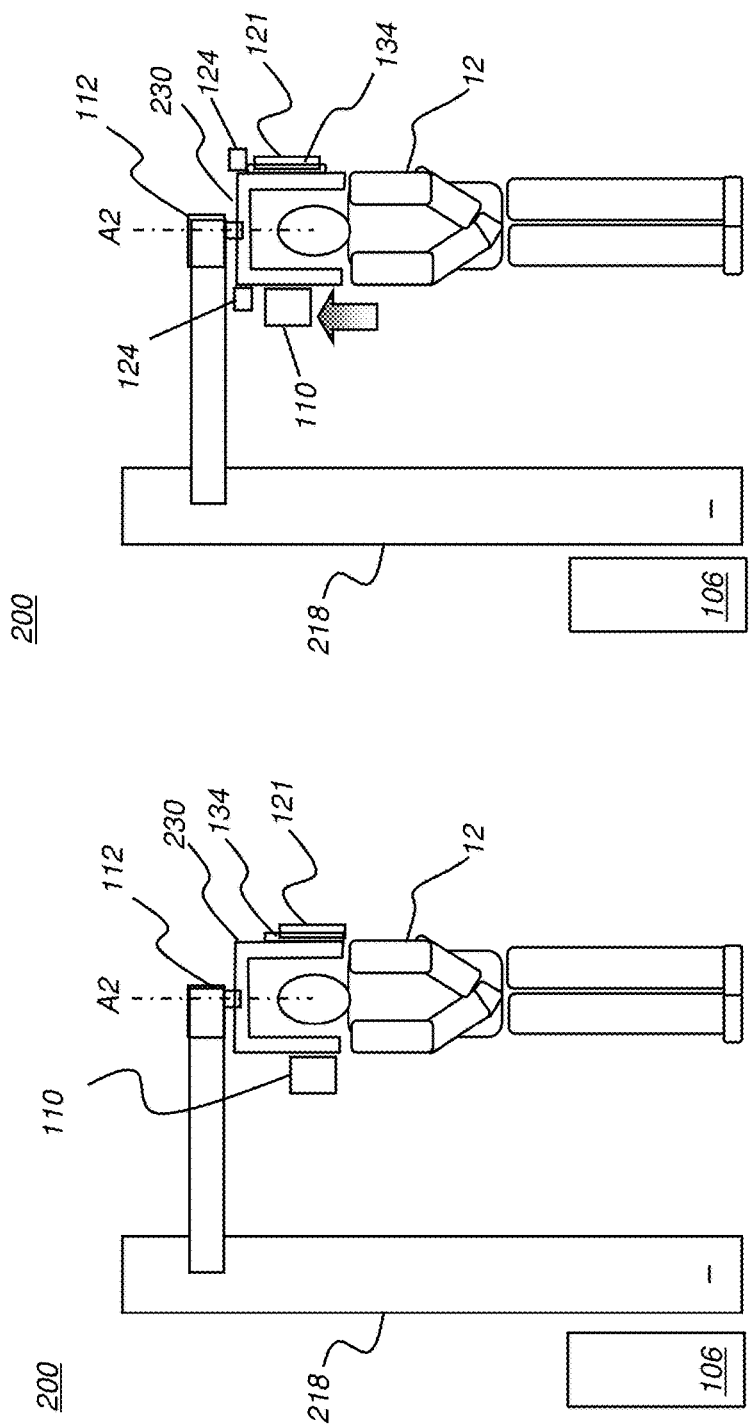

DENTAL IMAGING WITH PHOTON-COUNTING DETECTOR

CROSS REFERENCE TO RELATED APPLICATIONS

This application is a Continuation of earlier filed application U.S. Ser. No. 14/366,696, filed on Jun. 19, 2014, entitled "DENTAL IMAGING WITH PHOTON-COUNTING DETECTOR", in the names of Inglese et al., which is itself a is a 371 national stage application of earlier filed international application Serial No. PCT/US2012/043510, filed on 2012 Jun. 21, entitled "DENTAL IMAGING WITH PHOTON-COUNTING DETECTOR", in the names of Inglese et al., which application itself claims the benefit of earlier filed international application Serial No. PCT/US2011/066432, filed on 2011 Dec. 21, entitled "DIGITAL DETECTOR", in the names of Inglese et al., all of which are incorporated herein in their entirety.

FIELD OF THE INVENTION

The invention relates generally to the field of extraoral dental imaging and more particularly to apparatus and methods for obtaining volumetric images from the head of a patient.

BACKGROUND OF THE INVENTION

Radiological imaging is recognized to have significant value for the dental practitioner, helping to identify various problems and to validate other measurements and observations related to the patient's teeth and supporting structures. Among x-ray systems with particular promise for improving dental care is the extra-oral imaging apparatus that is capable of obtaining one or more radiographic images in a series and, where multiple images of the patient are acquired at different angles, combining these images to obtain a contiguous panoramic radiograph of the patient showing the entire dentition of the jaw, a tomographic image that contains more depth detail, or a computerized tomography (CT) volume image. To obtain images of any of these types, a radiation source and an imaging detector, maintained at a fixed distance from each other, synchronously revolve about the patient over a range of angles, taking a series of images by directing and detecting radiation that is directed through the patient at different angles of revolution.

Combination systems that provide both CT and panoramic x-ray imaging can include an X-ray source, an X-ray detector for detecting X-rays having passed through the subject, and supporting means for supporting the X-ray source and the X-ray detector so that they are spatially opposed to each other across the subject; and mode switching means for switching between a CT mode and a panorama mode. To detect X-rays, only one large area X-ray detector is used. The X-ray imaging apparatus can obtain both types of images by switching modes during the imaging session. However, the proposed imaging apparatus performs both CT and panoramic imaging using only one detector. This requires an expensive detector capable of carrying out both imaging functions in a satisfactory manner.

A combination imaging system can provide both CT and panoramic imaging using two separate sensors or detectors. By way of example, FIG. 1 in the present application shows a combined panoramic and CT imaging apparatus 40. A telescopic column 18 is adjustable for height of the subject. The patient 12 or other subject, shown in dotted outline, is positioned between an x-ray source 10 and an x-ray imaging sensor panel 20. X-ray imaging sensor panel 20 rotates on a rotatable mount 30 in order to position either a CT or a panoramic sensor 21 for obtaining the exposure. For CT imaging, CT sensor 21 is positioned behind the subject, relative to x-ray source 10. The operator rotates CT sensor 21 into this position as part of imaging setup. Similarly, the operator rotates panoramic sensor 21 into position behind the subject as part of the setup for a panoramic imaging session.

Another recent imaging system combines CT, panoramic, and cephalometric imaging from a single apparatus. For example, commonly assigned U.S. Patent Application Publication No. 2012/0039436 entitled "COMBINED PANORAMIC AND COMPUTED TOMOGRAPHY APPARATUS" to Bothorel et al. describes such a system.

A computerized tomography (CT) imaging apparatus operates by acquiring multiple 2 D images with a rotating imaging ensemble or gantry that has an x-ray source and, corresponding to (e.g., opposite) the x-ray source, an imaging sensor having a selectable spatial relationship (e.g., rotating about a fixed axis) relative to the patient. CT imaging allows the reconstruction of 3 D or volume images of anatomical structures of the patient and is acknowledged to be of particular value for obtaining useful information for assisting diagnosis and treatment.

Conventional digital radiography detectors have some limitations related to how attenuation of radiation energy at a single exposure is interpreted. For example, it can be very difficult, from a single exposure, to distinguish whether an imaged object has a given thickness or a given attenuation coefficient. To resolve this ambiguity, some systems provide separate, sequential low-energy and higher energy exposures and use the resulting difference in image information to distinguish between types of materials. However, in order to provide this information, this type of imaging requires that the patient be subjected to additional radiation for the second exposure. This problem can be compounded for CT imaging, in which multiple images are obtained, one from each of a number of angles of revolution about the patient.

Conventional CT imaging provides useful information that aids in diagnosis and treatment, but is constrained by limitations of the imaging sensor apparatus itself, and there are concerns over exposure levels needed for obtaining the desired image quality. There is room for improvement in system performance and in providing types of imaging that address practitioner interests with respect to a particular patient. Improvements are also needed for more accurate equipment positioning relative to the patient as well as for overall patient comfort. Additional improvements in image acquisition sequences and processing are also desired.

SUMMARY OF THE INVENTION

Accordingly, it is an aspect of this application to address in whole or in part, at least the foregoing and other deficiencies in the related art.

It is another aspect of this application to provide in whole or in part, at least the advantages described herein.

Embodiments of the present invention address the need for advancing the CT imaging art, particularly for imaging of the head. Embodiments of the present invention adapt photon-counting and related imaging solutions to the problem of CT imaging for dental, ENT, and related applications. Using embodiments of the present invention, a medical practitioner can obtain useful images for patient treatment, taking advantage of reduced exposure levels and other advantages that photon-counting solutions provide.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided an extra-oral dental imaging apparatus for obtaining an image from a patient, the apparatus comprising: a radiation source; a first digital imaging sensor that provides, for each of a plurality of image pixels, at least a first digital value according to a count of received photons that exceed at least a first energy threshold; a mount that supports the radiation source and the first digital imaging sensor on opposite sides of the patient's head; a computer in signal communication with the digital imaging sensor for acquiring a first two-dimensional dimensional image from the first digital imaging sensor; and a second digital imaging sensor that is alternately used (e.g., switched into place by the mount) and that provides image data according to received radiation.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 4B is a schematic view that shows a digital detector using a scintillator with a fiber optic array in conventional digital radiographic imaging.

FIG. 5 is a schematic view that shows a digital detector using a photon counting for digital radiographic imaging.

FIG. 11B shows the use of the detector positioning apparatus of FIG. 11A for CT imaging.

FIG. 11C shows the use of the detector positioning apparatus of FIG. 11A for panoramic imaging.

FIG. 12D shows the use of the detector positioning apparatus of FIG. 12A for cephalometric imaging.

FIGS. 16A and 16B show the imaging apparatus that provides a helical scan by changing the elevation of the digital sensor and radiation source during revolution about the patient.

DETAILED DESCRIPTION OF EXEMPLARY EMBODIMENTS

Figure 1:
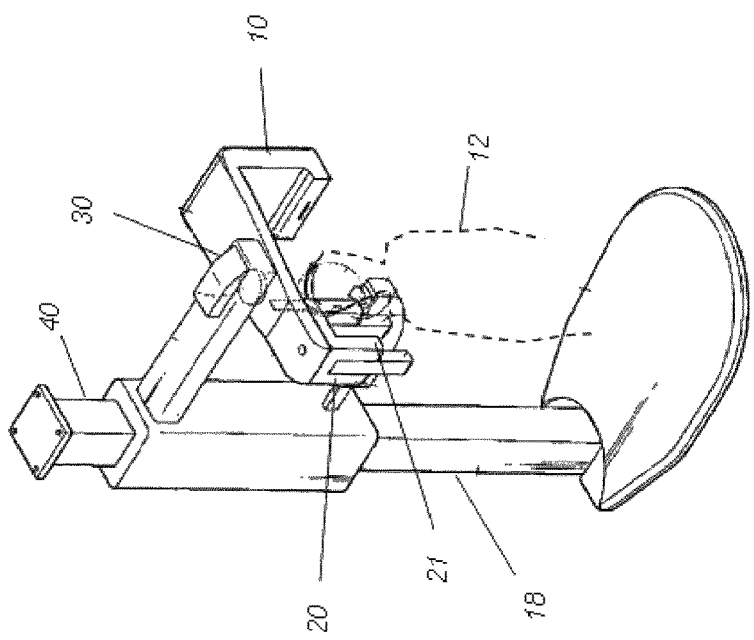
FIG. 1 shows a conventional CT imaging apparatus for dental or ear-nose-throat (ENT) imaging.

The following is a detailed description of the exemplary embodiments of the invention, reference being made to the drawings in which the same reference numerals identify the same elements of structure in each of the several figures.

According to certain exemplary embodiments, there is provided a radiographic imaging apparatus and/or methods (e.g., a dental, extra-oral dental) for obtaining an image based on received radiation (e.g., from a patient) that can provide the capability to obtain the image using at least one imaging modality (e.g., panoramic imaging, cephalometric imaging and CT imaging) and configured with at least one detector (e.g., sensor) of the photon counting type. When multiple imaging modalities are present in a single radiographic imaging apparatus, either additional detectors of the photon counting type or other types (e.g., CMOS-based, CCD-based, flat panel area detectors, sensors that use amorphous or polycrystalline semiconductor materials such as a-Si) can be used and/or at least one detector can be shared among at least two imaging modalities.

According to certain exemplary embodiments, the photon counting sensor can equip extraoral dental imaging device. In at least one embodiment, extra oral dental imaging devices can include at least one of a Computerized Tomography sensor, a panoramic sensor or a cephalometric sensor of the photon counting type. The cephalometric image acquisition method can be one shot or slot-scan.

For example, an extra oral dental imaging device can comprise two sensors, namely either a combination of a panoramic sensor and a CT sensor, a combination of a panoramic sensor and a cephalometric sensor or a combination of panoramic sensor and a CT sensor where at least one of the two sensors is the photon counting type. A device in which one single sensor is used for the two sensing functionalities can also be contemplated. In that case, the sensor is deplugged from a first position corresponding to a first imaging functionality and is plugged to a second position corresponding to a second imaging functionality.

Further, an extra oral imaging device comprising the three functionalities panoramic imaging, cephalometric imaging and CT imaging can also be contemplated, where at least one of the three imaging functionalities uses photon counting processes. In at least one embodiment, less than three sensors can be used for the three imaging functionalities. For example, at least one of the less than three sensors can be unplugged from a first position and plugged in a second position.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional volume images and a pixel for 2-dimensional images. Volume images, such as those from CT or CBCT apparatus, are formed by obtaining multiple 2-D images of pixels, taken at different relative angles, then combining the image data to form corresponding 3-D voxels. For the purposes of the description herein, the terms voxel and pixel can generally be considered equivalent, describing an image elemental datum that is capable of having a range of numerical values. Voxels and pixels have attributes of both spatial location and image data code value.

In the context of the present disclosure, the term "code value" refers to the value that is associated with each volume image data element or voxel in the reconstructed 3-D volume image. The code values for CT images are often, but not always, expressed in Hounsfield units (HU).

In the context of the present invention, the terms "digital sensor" or "sensor panel" and "digital detector" are considered to be equivalent. These describe the panel that obtains image data in a digital radiography system. The term "revolve" has its conventional meaning, to move in a curved path (e.g., 3 D) or orbit around a center point (e.g., fixed or movable).

In the context of the present disclosure, the terms "operator", and "user" are considered to be equivalent and refer to the operating practitioner, technician, or other person who views and manipulates an x-ray image or a volume image (e.g., formed from a combination of multiple x-ray images) at an image acquisition apparatus (e.g., on a display monitor). A "technician instruction" or "operator command" can be obtained from explicit commands entered by the user or may be implicitly obtained or derived based on some other user action, such as making a collimator setting, for example. With respect to entries on an operator interface, such as an interface using a display monitor and keyboard, for example, the terms "command" and "instruction" may be used interchangeably to refer to an operator entry.

In the context of the present disclosure, the terms "viewer" can refer to the viewing practitioner (e.g., radiologist), technician, or other person who views and manipulates an x-ray image or a volume image that is formed from a combination of multiple x-ray images, on a display monitor away form the image acquisition apparatus. A "viewer instruction" can be obtained from explicit commands entered by the viewer or may be implicitly obtained or derived based on some other action.

In order to more fully understand aspects of the present invention, it is instructive to consider different approaches used for CT imaging in conventional practice and to compare these with aspects of CT and other volume imaging modes according to embodiments of the present invention. By way of example, FIG. 1 shows an embodiment of a conventional CT imaging apparatus 40 for dental imaging. A column 18 is adjustable for height of the subject. The patient 12 or other subject, shown in dotted outline, is positioned between an x-ray source 10 and an x-ray imaging sensor panel 20, also termed an imaging detector. X-ray imaging sensor panel 20 rotates on a rotatable mount 30 in order to position a CT sensor 21 for obtaining the exposure. CT sensor 21 is positioned behind the subject, relative to x-ray source 10. The operator rotates CT sensor 21 into this position as part of imaging setup. With rotation of mount 30, sensor 21 and source 10 revolve about the head of the patient, typically for some portion of a full revolution.

Figure 2:
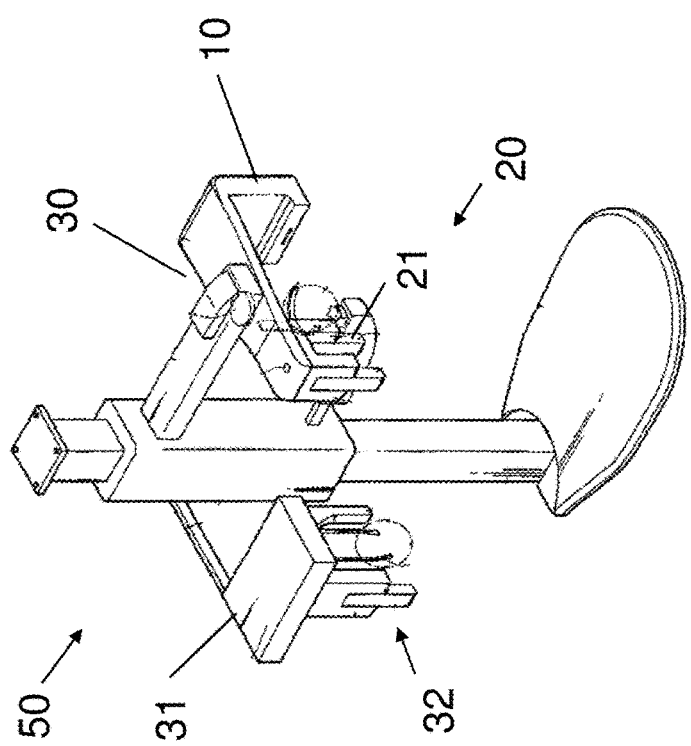
FIG. 2 shows an imaging apparatus that provides both CT and panoramic x-ray imaging and adds cephalometric imaging capability.

Other imaging system solutions provide additional types or modes of imaging in addition to CT imaging and thus enable switching between various imaging modes. FIG. 2 shows an embodiment of an imaging apparatus providing combined panoramic, CT, and cephalometric imaging. An imaging apparatus 50 has similar radiation source and sensor components to the earlier system of FIG. 1, provided on rotatable mount 30. In addition, a cephalometric imaging system 31 is mounted on a separate arm 32.

Figure 3:
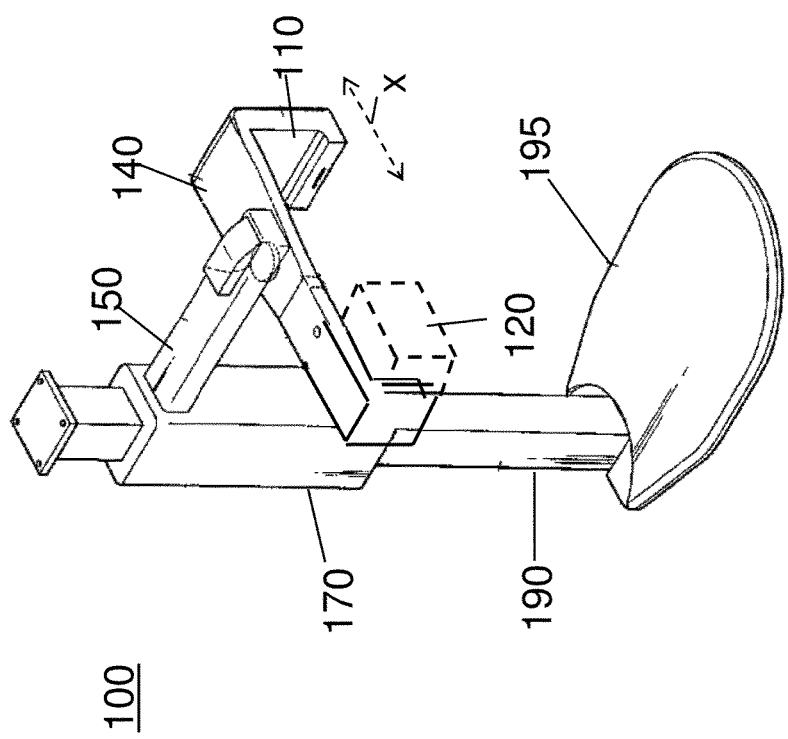
FIG. 3 shows an imaging apparatus according to an embodiment of the present invention.

Referring to the perspective view of FIG. 3, a combined imaging apparatus 100 for panoramic, computed tomography and cephalometric imaging has a base 195, a support pole 190, and an elevation member 170 mounted on support pole 190. Elevation member 170 adjusts over a range of vertical positions to adapt for patient height. A rotary arm supporting member 150 extends from an upper portion of elevation member 170. A rotary arm 140 is supported by rotary arm supporting member 150 and provides, at one end, an x-ray source 110 that is energizable to provide exposure radiation along an exposure path and, at the other end, an x-ray detector apparatus 120. X-ray source 110 is in a fixed position relative to rotary arm 140 in one embodiment. In an alternate embodiment, x-ray source 110 can be separately mounted and moved toward or away from x-ray detector apparatus 120, in the x-direction as noted in FIG. 3. Not shown in FIG. 3, but required for an imaging apparatus of this type, is the needed support apparatus for providing power, data connection, and other functions.

Windowing can alternately be used for obtaining image content that can be used for reconstructing the volume image. According to an embodiment of the present invention, a movable slit translates along the surface of the imaging sensor to provide a scan of the image content. This slit can be provided by the collimator, for example, or by some alternate device or may be digitally simulated. Alternately, movement of the imaging sensor itself is used to determine the imaged area. In certain exemplary embodiments, windowing can be provided by control of at least one selected portion (e.g., square, slit, prescribed area, prescribed subset) of the sensor (e.g., pixels) that are configured to be read out to generate an image (e.g. based on radiation received). The selected portion (e.g., the window) can correspond to a capability of an imaging system or an examination type and can be implemented by hardware, software or a combination thereof.

Other types of image acquisition and processing can alternately be performed using the same basic system, including 2-D image acquisition, partial CT imaging, transverse imaging (in which the layer of interest is orthogonal to the panoramic layer), SPECT (Single-Photon Emission Computerized Tomography) scanning, linear tomographic imaging, and others.

Photon-Counting Detector Operation and Data Acquisition

For each of the embodiments shown in FIGS. 1-3, a sensor panel is used as the digital detector for receiving the exposure and generating the image data. For embodiments of the present invention, one or more of the sensor panels that is used for acquiring data is a photon-counting image detector.

Figure 4A:
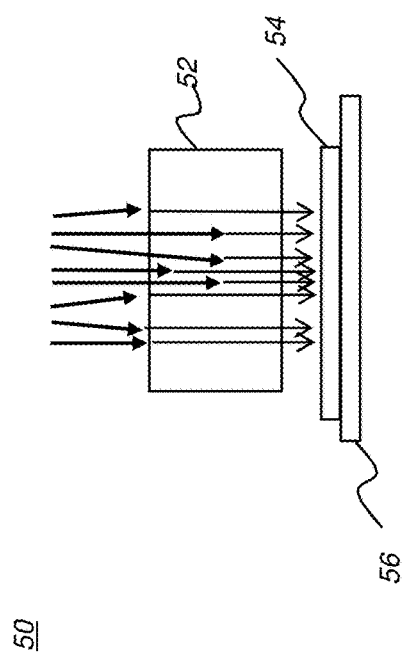
FIG. 4A is a schematic view that shows a digital detector using a scintillator in conventional digital radiographic imaging.

FIGS. 4A through 4D schematically illustrate different approaches to radiologic imaging that can be employed for CT systems. FIG. 4A shows elements of an x-ray imaging sensor 50 that uses an indirect imaging method for generating image data in response to radiation through a patient or other subject. In this model, x-ray photons are incident on an x-ray converting element 52 that converts the energy from ionizing x-ray radiation to visible light or other light energy. X-ray converting element 52 is commonly referred to as a scintillator. An energy detecting element 54, mounted on a support structure 56, then detects the converted energy, such as using an array of photocells. The photocells can be light-sensitive CMOS (Complementary Metal-Oxide Semiconductor) components formed in an array as a semiconductor chip and providing a signal corresponding to each detected image pixel.

Figure 4C:
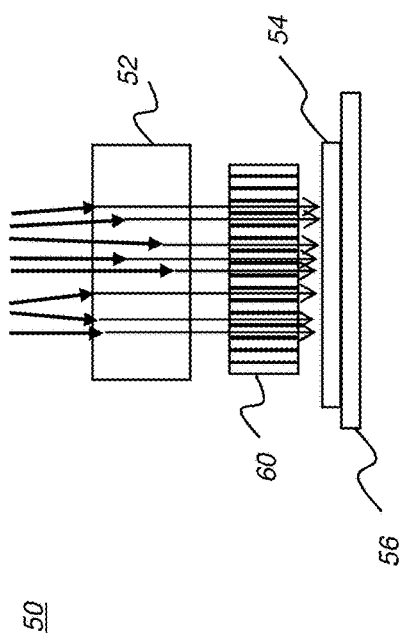
FIG. 4C is a schematic view that shows a digital detector using a thicker scintillator with a fiber optic array in conventional digital radiographic imaging.

Scatter, resulting in cross-talk between pixels and consequent loss of some amount of resolution, is one acknowledged problem with the basic approach shown in FIG. 4A. The modification of FIG. 4B addresses this problem by adding a fiber-optic array 60 between the scintillator or x-ray converting element 52 and energy detecting elements 54. FIG. 4C shows another modification that can help to improve sensitivity to radiation, enlarging the width of the scintillator or x-ray converting element 52; however, this solution can result in some loss of sharpness in the obtained image.

Figure 4D:
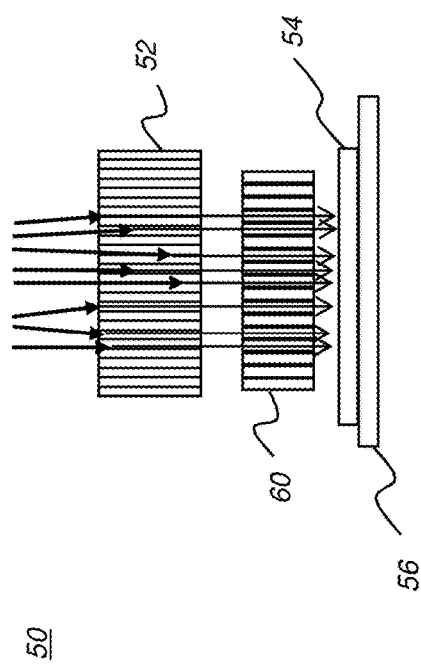
FIG. 4D is a schematic view that shows a digital detector using a structured scintillator with a fiber optic array in conventional digital radiographic imaging.

FIG. 4D shows the use of a structured scintillator serving as x-ray converting element 52. The structured scintillator can use a material such as cesium iodide (CsI), although this material is structurally fragile and has some limitations with respect to image quality. This modified scintillator type can be used in addition to fiber-optic array 60 as shown in FIG. 4D for some improvement in performance.

The conventional model shown in FIG. 4A and improvements outlined with respect to FIGS. 4B, 4C, and 4D provide a reasonable level of imaging performance for CT imaging applications. However, even with the added cost and complexity of the additional components and features used, only incremental improvements in image quality and overall performance are achieved.

An alternative approach to image capture using a direct imaging method is shown in FIG. 5. An imaging sensor 70 using direct detection has a direct detection element 72, such as a semiconductor or other sensitive material that converts incident x-ray photons to an electron flow. The excited electrons are then accelerated by an electrical field F and are sensed by an electron-sensitive CMOS array that acts as energy detecting element 54. Advantageously, with direct detection imaging sensor 70, each incoming x-ray photon is much more likely to be detected than with indirect imaging devices. This increases the DQE (detective quantum efficiency), a performance metric for an imaging detector. Reduced scatter, a result of the electric field that guides electron charge toward the CMOS array elements, makes this approach more efficient, improves resolution, and provides a more favorable signal-to-noise (S/N) ratio. As a result, lower levels of ionizing radiation can be used for obtaining an image with direct detection imaging sensor 70. The needed threshold values are within or below the range needed with the more conventional indirect devices described with reference to FIGS. 4A-4D. Direct-detection semiconductors used for direct detection element 72 can include polycrystalline or monocrystalline materials. Monocrystalline materials are advantaged over polycrystalline for ease of fabrication and handling; however, there are size constraints to detectors formed from monocrystalline materials. Polycrystalline materials are more difficult to fabricate and handle, but are capable of providing larger detectors. Candidate materials for this purpose include cadmium telluride (CdTe or CadTel), lead iodide ($PbI_2$), lead oxide (PbO), and mercuric iodide ($HgI_2$), and types of poly crystal, amorphous Selenium (aSe), and other materials.

Figure 6:
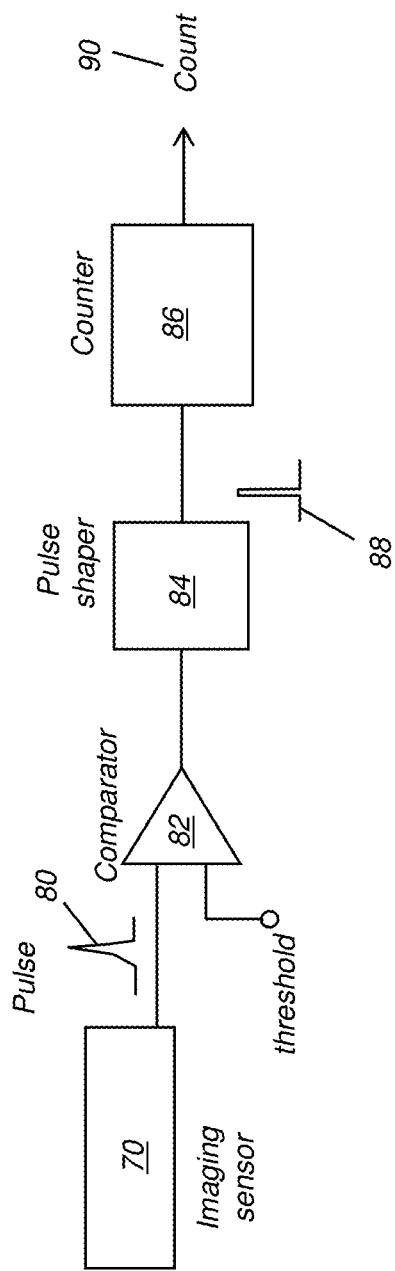
FIG. 6 is a schematic diagram that shows the image processing chain for each pixel of the digital detector when using photon counting.

Another distinction is made between how x-ray detectors record and report the received energy. Integrating x-ray sensors are spatially digitized and provide an analog output that represents the accumulated charge received for each pixel during the exposure. High noise levels can be a problem with integrating sensors. Another approach is commonly termed "photon-counting". In this alternative method, each incoming photon generates a charge, and each of these events is reported or counted. The actual count of photons, or a value that is computed according to the count, is provided as the image data for each pixel. Advantageously, photon counting has high immunity to noise, provided that pulse strength exceeds background noise levels. FIG. 6 shows the photon-counting sequence in schematic form. An incoming photon generates a pulse 80 at a given energy level. The pulse 80 energy is compared against a threshold value at a comparator 82 and shaped in a pulse shaper 84 to form a shaped pulse 88. A counter 86 then records the pulse event and provides a digital output, a pulse count value 90. A separate pulse count value 90 is obtained for each pixel element in imaging sensor 70. The threshold value can be adjustable or selectable from a range of values, depending on the photon energies of interest.

A further advantage of pulse counting relates to its capability to count pulses 80 at multiple threshold values.

Figure 7:
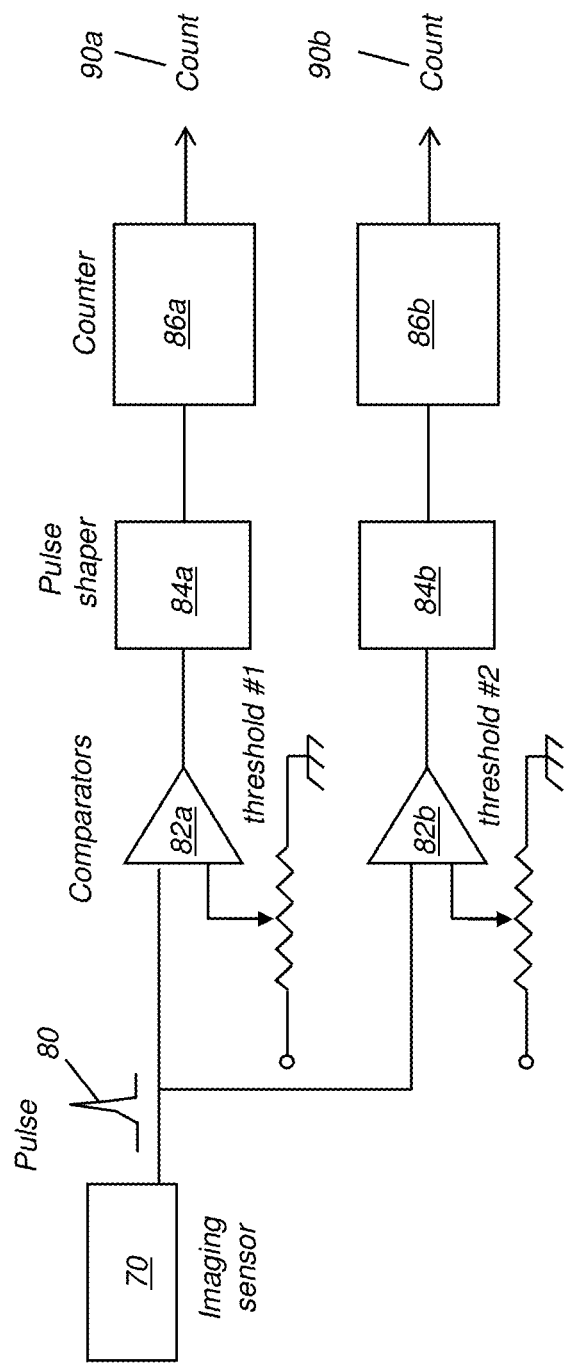
FIG. 7 is a schematic diagram that shows the image processing chain for each pixel of the digital detector using multiple thresholds when using photon counting.

Referring to the schematic diagram of FIG. 7, two comparators 82a and 82b are shown for measuring pulse energy. In this particular configuration, a comparator 82a, a pulse shaper 84a, and a counter 86a provide a count 90a value for all pulses above a first threshold; similarly, a comparator 82b, a pulse shaper 84b, and a counter 86b account for only pulses above a higher, second threshold and provide a count 90b accordingly. Simple subtraction then identifies the different power levels achieved for each pulse. It can be appreciated that more than two threshold levels can be measured, using a corresponding arrangement of comparator circuitry that follows the model that is shown in FIG. 7, allowing pulse counts at any of a number of threshold values. In addition, thresholds can be selectable, such as adjustable to adjust the response of imaging sensor 70 to various photon energy levels. Thus, for example, an operator can use a set of preset thresholds for differentiating softer from denser tissue in the image that is finally generated.

In addition to setting minimum thresholds, embodiments of the present invention also provide the option of using upper or maximum thresholds for photon energy. This capability can be used for a number of functions, including reducing the effects of radiation on semiconductor components and reducing generation of excessive noise signals.

Figure 8A:
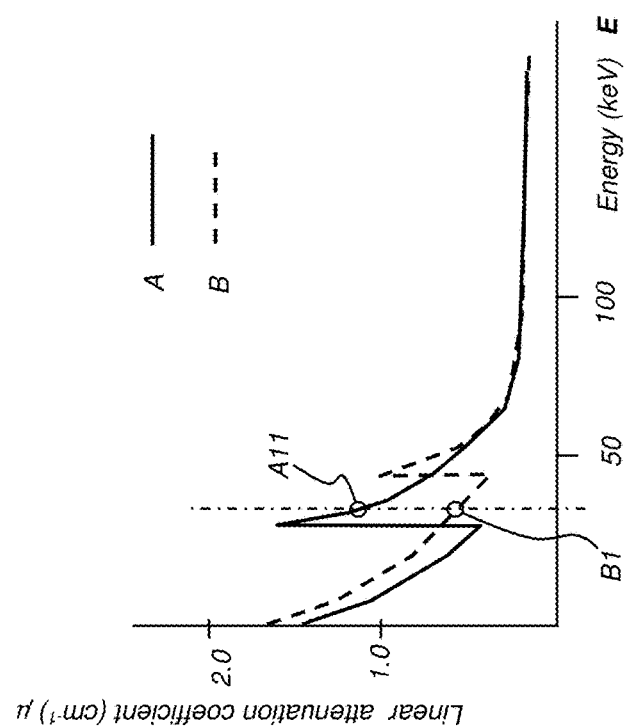
FIG. 8A is a graph that shows linear attenuation characteristics at different energy levels for two exemplary metallic materials.
Figure 8B:
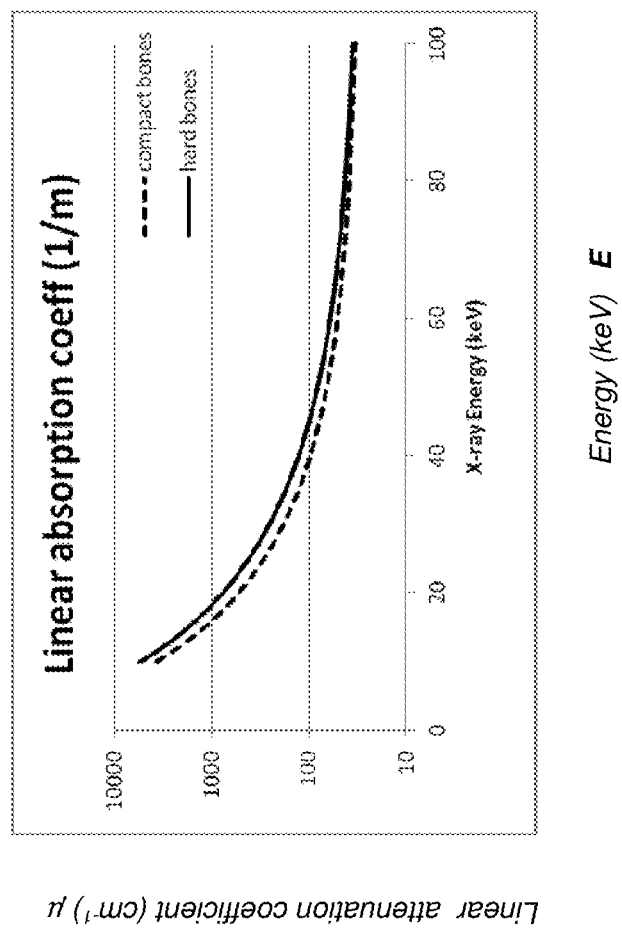
FIG. 8B is a graph that shows the linear absorption coefficient for different types of bone tissue.

The capability to count photons at different energy thresholds, as described with reference to FIG. 7, allows the sensor to differentiate between energy levels obtained from irradiating the subject and provides added dimension to the image data that is provided as a result of each exposure. This capability, described as multi-spectral or "color" x-ray imaging, enables information to be obtained about the material composition of a subject pixel. As shown for typical metals in the simplified graph of FIG. 8A, two materials A and B have different coefficients of attenuation μ that vary with the level of radiation energy, shown as exposure E. At a given exposure, material A attenuates a photon with an energy that corresponds to material A, as shown at value A11. Similarly, radiation impinging on material B attenuates a photon with an energy that corresponds to material B, as shown at value B1. Where photons of these different energy values can be differentiated from each other, it is possible to identify one or both materials in the same pixel or voxel image element of the obtained image. This same basic behavior in response to radiation also allows some measure of capability to differentiate tissue types. By way of example, the graph of FIG. 8B shows relative coefficients of attenuation for different bone densities. As FIG. 8B suggests, different linear absorption characteristics allow differentiation between various types of tissue, such as between bone types.

The use of multi-spectral or "color" x-ray imaging can have a number of potential benefits of value for dental, ENT, and head imaging. These include minimization of metal artifacts, separate reconstruction of soft and hard tissue, more efficient segmentation algorithms for tooth and bone features, improved pathology detection for cancer and other disease, and detection of trace materials or contrast agents.

In addition to opportunities for improvement in the image processing chain, there are a number of differences in structure, operation, scanning sequence, dimensions, and supporting hardware that are needed to provide the advantages of photon counting in embodiments of the present invention. As one significant difference from conventional large-area image detection, the photon-counting architecture results in an image detector of reduced size, generally requiring a scanning sequence even where only a 2-D image is obtained. For volumetric imaging, such as in the sequence needed for CT or for cone-beam CT (CBCT) imaging, it may be necessary not only to scan within the same plane, but to provide a 3-dimensional helical scan.

According to an embodiment of the present invention, a photon-counting sensor is provided as a retrofit to an existing panoramic imaging apparatus in order to provide additional capability, such as for CT imaging, for example. Retrofit can be performed by the operator as needed by manually switching the detector type at the time of image acquisition.

According to an embodiment of the present invention, the x-ray imaging sensor has an active area with a long dimension that exceeds its short dimension by more than 1.5.

The photon-counting detector can be linear or rectangular, as well as of some other shape, such as an irregular shape, for example. Portions of the detector can be selectively enabled or disabled according to the imaging type that is needed. Thus, for example, an imaging sensor can be rectangular in shape, but use only a line, slot, polygon, curved set or designated subset of pixels at a time for a particular type of sensing. Other shape variations are possible, with various portions of an irregularly shaped detector selectively enabled or disabled according to the profile of the anatomy that is being imaged.

During exposure of the patient, the x-ray source can be pulsed or continuous and may change its exposure levels from one exposure to the next. A helical or horizontal scan pattern can be used. Collimator movement may be provided during the imaging sequence to direct radiation toward the area of interest.

Setup, Alignment, and Positioning

As described with reference to FIGS. 1-3, the patient or other subject to be imaged is positioned between x-ray source 110 and x-ray detector apparatus 120, as shown in more detail subsequently. As is familiar to those skilled in the diagnostic imaging arts, a number of patient support devices, not specifically shown in FIG. 3 but described in more detail subsequently, may also be provided for helping to stabilize and position the head of the patient, including a chin supporting member, for example.

Figure 9A:
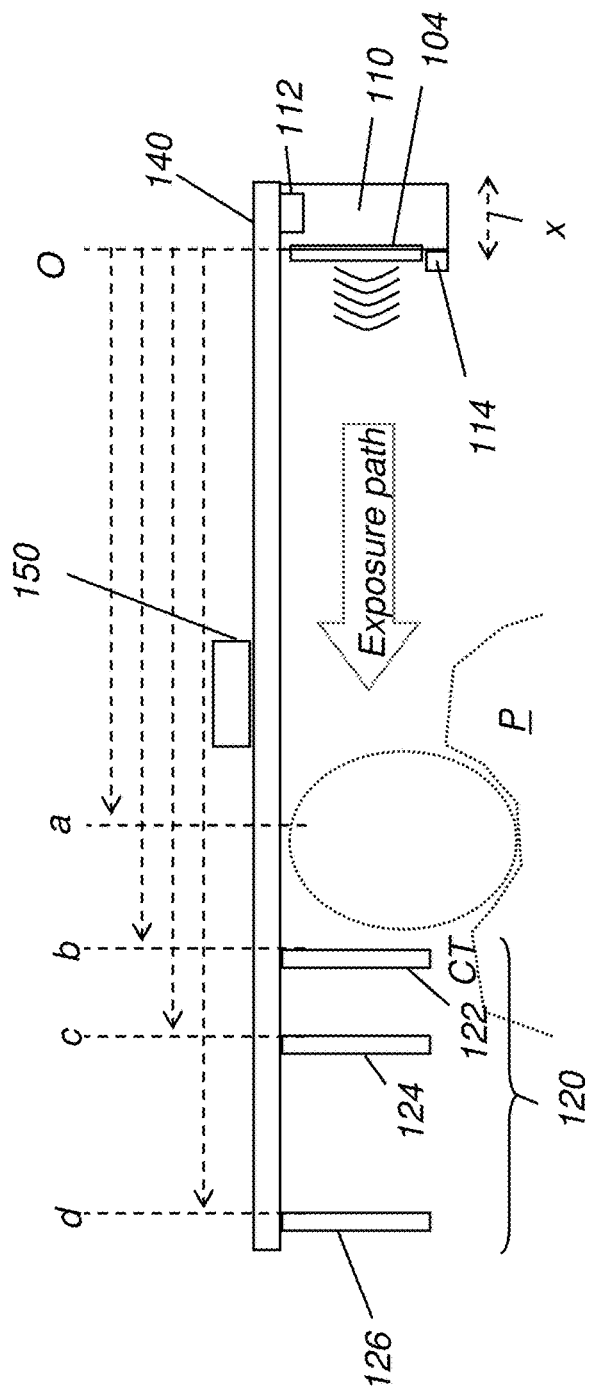
FIG. 9A shows a schematic view of source-to-detector distances that apply for each type of imaging that is performed by apparatus of the present invention.
Figure 9B:
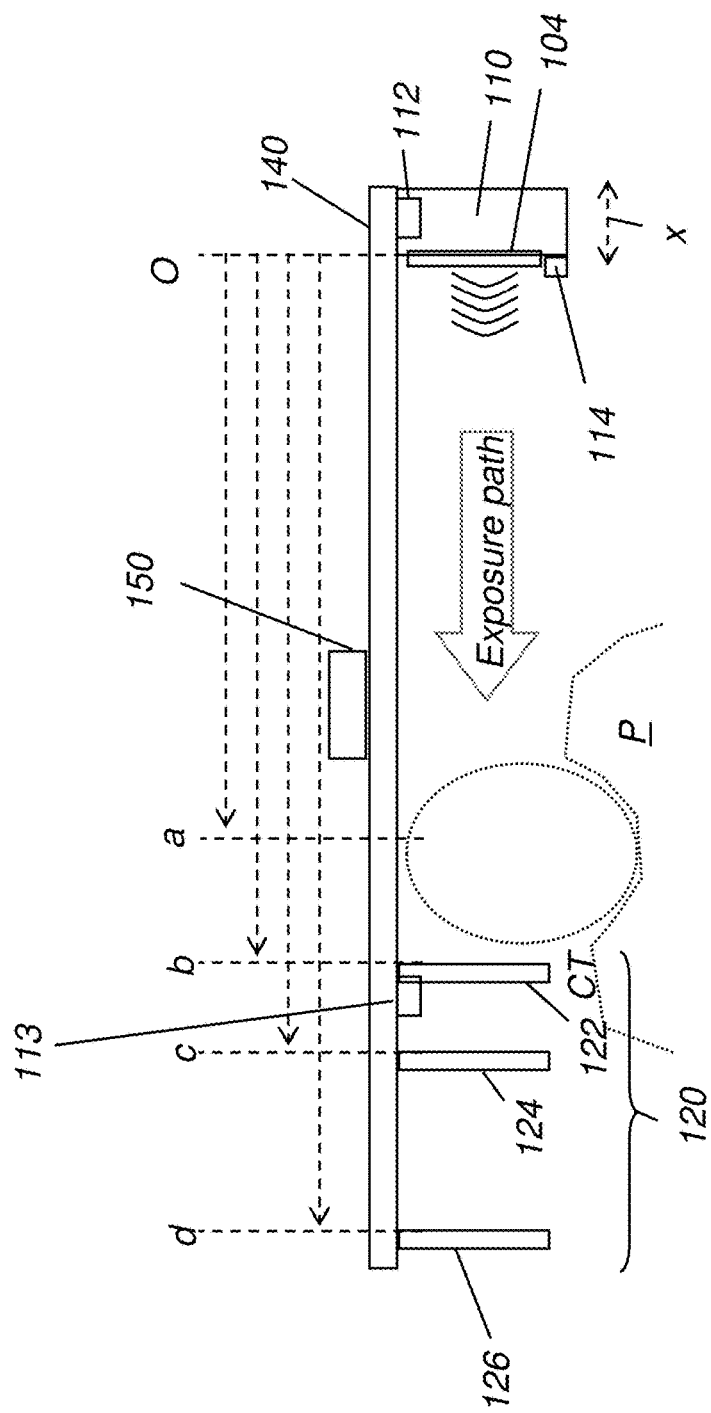
FIG. 9B shows a schematic view with variable source-to-detector distances for different imaging modes.

FIG. 9A is a schematic view of source-to-detector distances along an exposure path from x-ray source 110, at a position labeled O, that apply for each type of imaging that can be performed by apparatus of embodiments of the present invention. Three detector components within rotary arm 140 are shown: a CT detector 122 at a distance Ob along the exposure path from x-ray source 110, a panoramic detector 124 at a distance Oc, and an optional cephalometric detector 126 at a distance Od. Distances Ob, Oc, and Od can vary for each different type of imaging that is performed, based on factors such as detector size, needed magnification ratio, relative position of the subject, collimation, and other factors related to x-ray imaging. The relative position of a subject, shown as patient P, in the exposure path with respect to x-ray source 110 and to the various detectors 122, 124, and 126 is represented in dotted outline. The exposure path extends horizontally, in the x-direction as shown in FIG. 9, along the rotary arm 140. Collimation at x-ray source 110 is used to substantially constrain exposure radiation to this linear path. An optional source translation apparatus 112 can be provided for moving x-ray source 110 in the proper direction along or orthogonal to the horizontal x-axis as shown. FIG. 9B shows an embodiment that is capable of moving the position of either source 110 or detector 122 using a detector translation apparatus 113. Shown subsequently are various arrangements of components that are used for positioning the desired detector 122, 124, or 126 in place for each type of imaging that is performed. As noted earlier, one or more of detectors 122, 124, and 126 is a photon-counting detector according to an embodiment of the present invention.

Figure 10A:
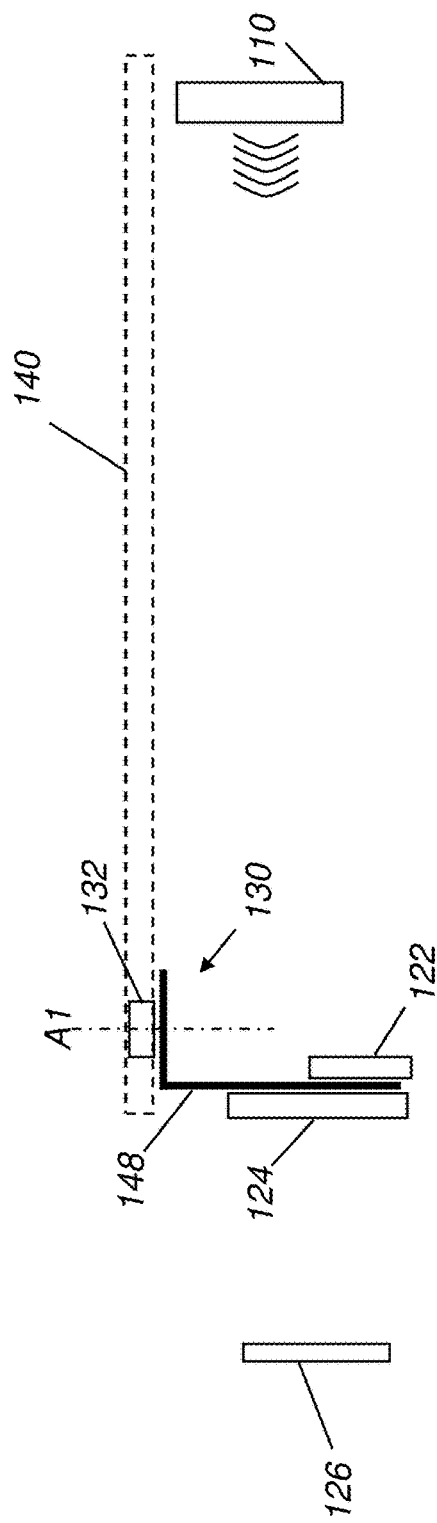
FIG. 10A shows an embodiment of a three-position detector positioning apparatus.

Referring to FIGS. 10A-10D, there is shown an arrangement for positioning, supporting, and moving the various CT, panoramic, and cephalometric detectors 122, 124, and 126 of FIG. 9 according to one embodiment. FIG. 10A is a side view that shows a three-position detector positioning apparatus 130 with a movable platen 148 that is used to mount CT and panoramic detectors 122 and 124 adjacently, either back to back as shown in FIGS. 10A-10D, or side-by-side as shown in FIGS. 11A-11D. In the context of the present disclosure, a platen is considered to be a single protruding support element that extends in a direction that is orthogonal to the length of rotary arm 140. For reference, the relative position of rotary arm 140 is shown in dashed line form in FIGS. 10A and 11A. The platen itself could be in the form of a plate or other structure that provides one mounting surface or two mounting surfaces that are substantially in parallel. The platen is movable as a single element to provide rotational or other curvilinear translation of its corresponding detectors and could have variable thickness.

Figure 10B:
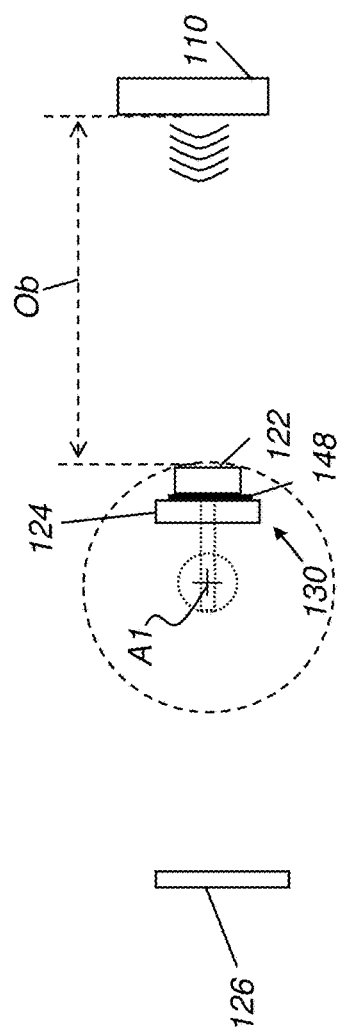
FIG. 10B shows the use of the detector positioning apparatus of FIG. 10A for CT imaging.
Figure 10C:
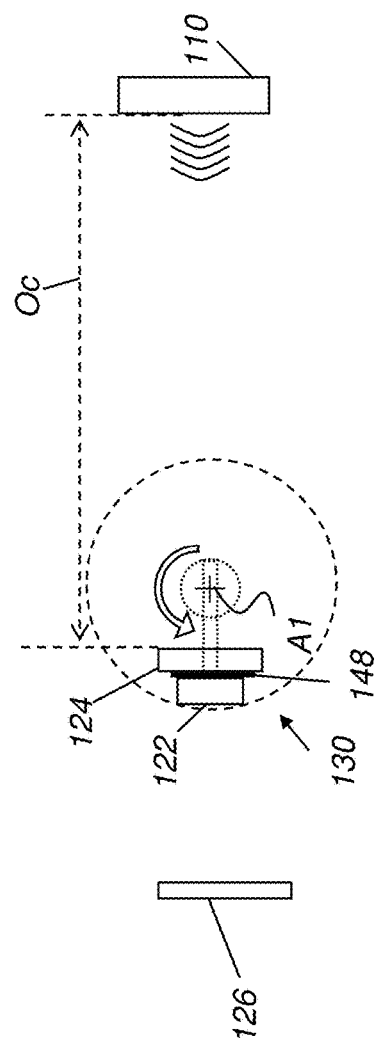
FIG. 10C shows the use of the detector positioning apparatus of FIG. 10A for panoramic imaging.
Figure 10D:
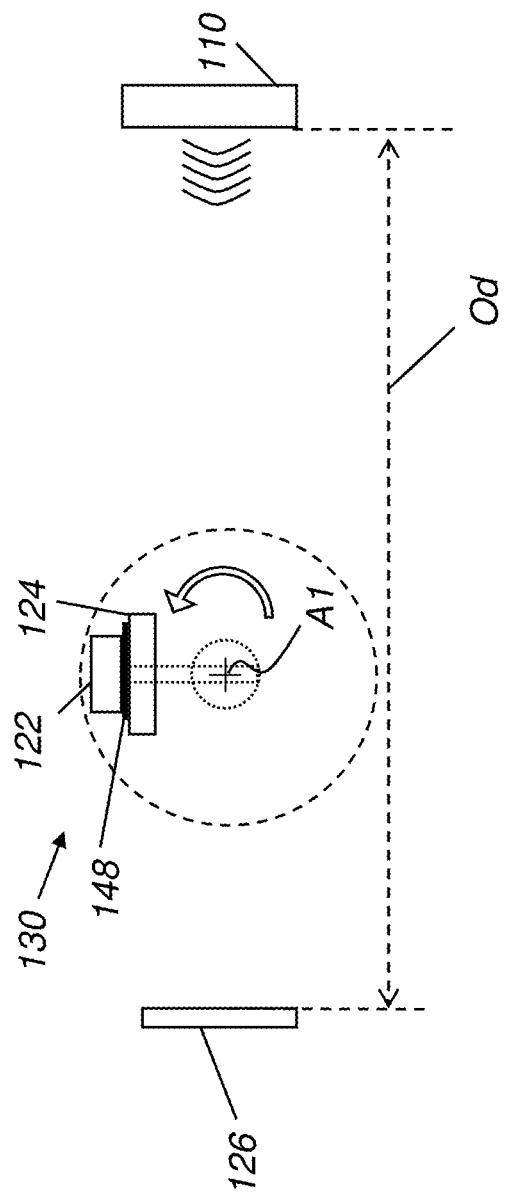
FIG. 10D shows the use of the detector positioning apparatus of FIG. 10A for cephalometric imaging.

CT and panoramic detectors 122 and 124 mount back-to-back on a movable platen 148 in the FIG. 10A embodiment. Movable platen 148, driven by a drive 132, rotates about a vertical rotation axis A1 to a suitable position for each of the two or three imaging types. Axis A1 is substantially orthogonal to the length of rotary arm 140, as shown in the FIG. 10A embodiment. FIGS. 10B, 10C, and 10D are each top views, taken along rotation axis A1 to show detector positioning for each of three detector types. FIG. 10B shows a top view with movable platen 148 of detector positioning apparatus 130 translated to a first position for CT imaging. In this configuration, CT detector 122 is properly positioned on the direct path of, unobstructed with respect to, and in line with, x-ray source 110 at distance Ob. FIG. 10C shows a top view with movable platen 148 of detector positioning apparatus 130 rotated to a second position for panoramic imaging. In this next configuration, panoramic detector 124 is positioned at distance Oc along the exposure path and is in the direct path of, unobstructed with respect to, and in line with x-ray source 110. FIG. 10D shows a top view with movable platen 148 of detector positioning apparatus 130 moved to a third position for cephalometric imaging, translated to displace detectors 122 and 124 so that they are out of the exposure path between x-ray source 110 and cephalometric detector 126. In this third position, cephalometric detector 126 is unobstructed with respect to, in the direct path of, and in line with x-ray source 110. In the FIG. 10A-10D embodiment, rotational translation of the movable platen between first and second positions is with respect to a vertical axis or, more generally, to an axis that is orthogonal to the length of rotary arm 140. Other sensor arrangements that allow rapid switching between sensors include back-to-back configurations that rotate a shaft or other device that runs between two back-to-back sensors.

In another embodiment, a radiographic imaging apparatus for obtaining an image based on received radiation (e.g., from a patient) can provide the capability to obtain the image using two different imaging modalities such as panoramic imaging and cephalometric imaging, for example of the slot-scan type, by sharing a single photon counting detector. For example, the single photon counting detector can be moved reciprocally between a first position to receive radiation generated by a panoramic imaging event and a second position to receive radiation generated by a cephalometric imaging event. Such reciprocal movement can be implemented by an operator (e.g., physically moving the photon counting sensor between the first and second position), the operator using mechanical apparatus or electro-mechanical apparatus, automatically (e.g., based on imaging modality selected) or the like. In one embodiment, different portions of the single photon counting sensor (e.g, set of pixels) can be used for different imaging modalities (e.g., slot having a length/width ratio >2 or a prescribed number, or approximately square having a length/width ratio <1.4 or a prescribed number.

Figure 11A:
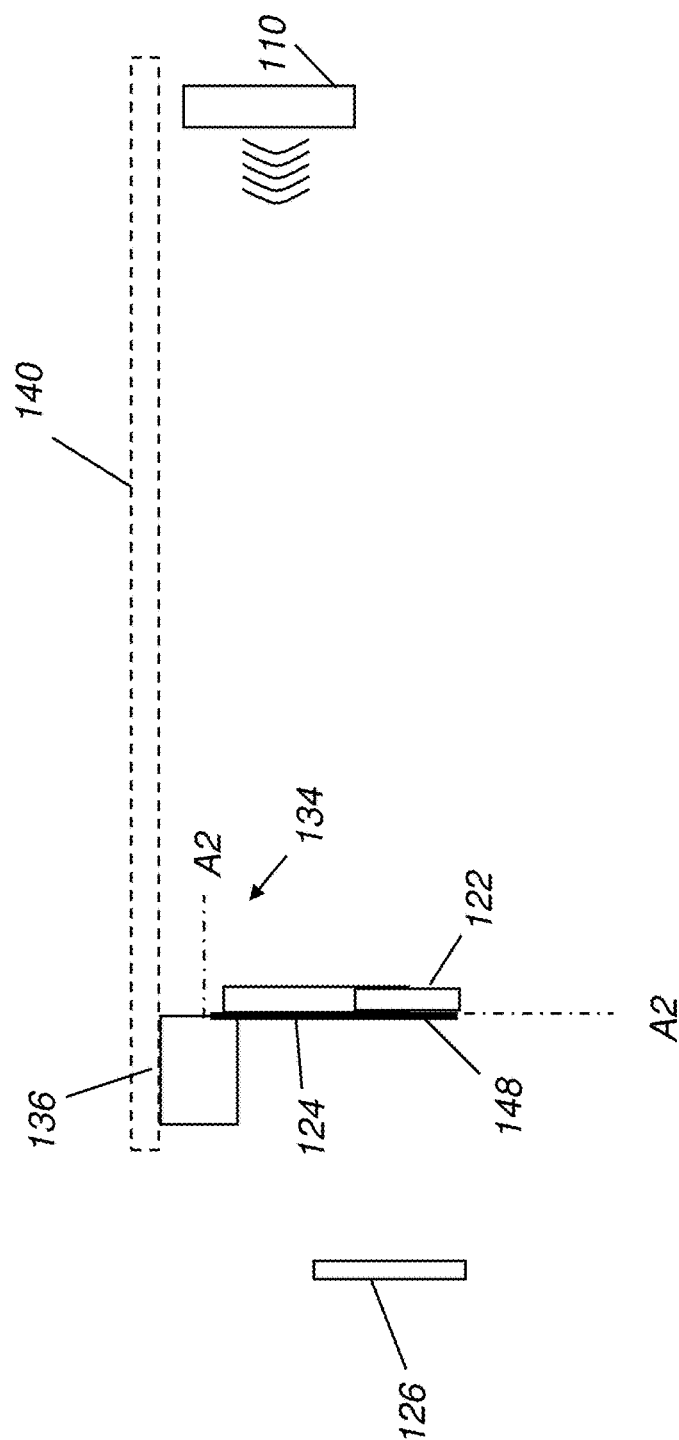
FIG. 11A shows an alternate embodiment of a three-position detector positioning apparatus.
Figure 11D:
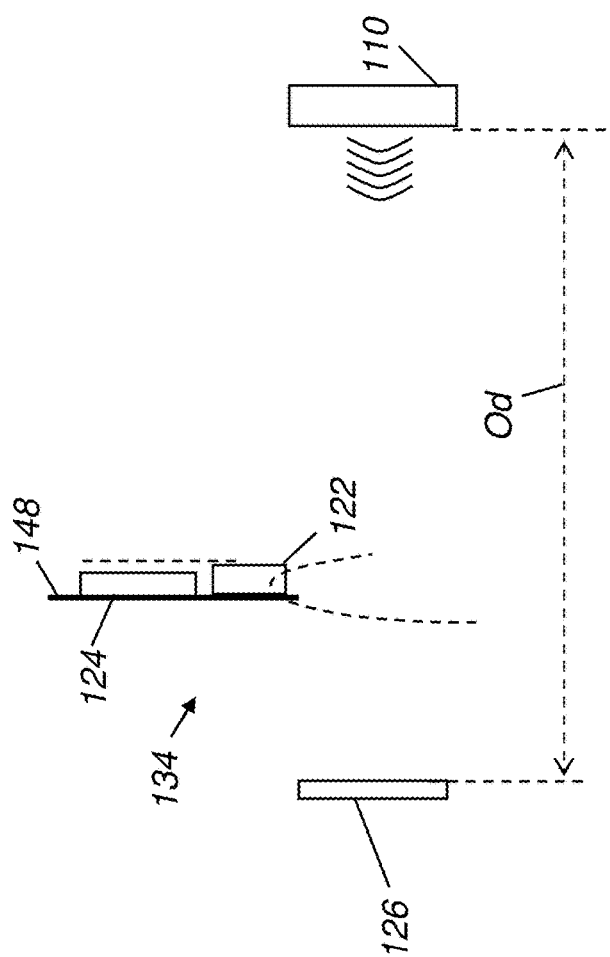
FIG. 11D shows the use of the detector positioning apparatus of FIG. 11A for cephalometric imaging.

Referring to FIGS. 11A-11D, there is shown an alternate embodiment for positioning, supporting, and moving the various CT, panoramic, and cephalometric detectors 122, 124, and 126. In this embodiment, detectors 122 and 124 mount adjacently, such as side-by-side or top-to-bottom, on the same side of movable platen 148. Movable platen 148 translates detector position relative to the plane of the platen, shown for reference as Q in FIG. 11A. FIG. 11A is a side view that shows a three-position detector positioning apparatus 134 having an x-y translation drive 136 for detector positioning. Detector positioning apparatus 134 provides a curvilinear translation path for the detectors in a plane orthogonal to an axis A2 that is substantially parallel to the length of rotary arm 140. FIGS. 11B, 11C and 11D are each top views showing detector positioning for each of three detector types. FIG. 11B shows a top view with movable platen 148 of detector positioning apparatus 134 translated to a first position for CT imaging. In this configuration, CT detector 122 is properly positioned at distance Ob along the exposure path, unobstructed with respect to, and in the direct path of x-ray source 110. FIG. 11C shows a top view with movable platen 148 of detector positioning apparatus 134 translated to a second position for panoramic imaging. In this configuration, panoramic detector 124 is positioned at distance Oc along the exposure path, unobstructed with respect to, and in the direct path of x-ray source 110. Distances Ob and Oc can be the same in this embodiment. FIG. 11D shows a top view with movable platen 148 of detector positioning apparatus 134 moved to a third position for cephalometric imaging, with movable platen 148 translated to remove detectors 122 and 124 out of the path between x-ray source 110 and cephalometric detector 126 so that cephalometric detector 126 is unobstructed with respect to, and in the direct path of x-ray source 110. In the FIG. 11A-11D embodiment, curvilinear translation of the movable platen between first and second positions is in a plane that is orthogonal with respect to the length of rotary arm 140. Curvilinear translation within the plane can be provided by a rotary actuator or by one or more linear actuators, for example.

Figure 12A:
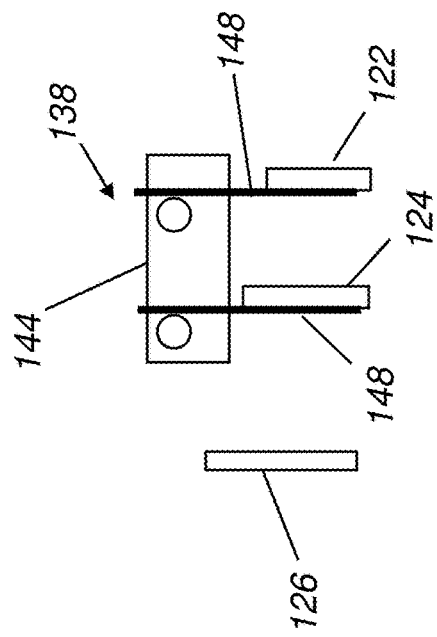
FIG. 12A shows another alternate embodiment of a three-position detector positioning apparatus.
Figure 12B:
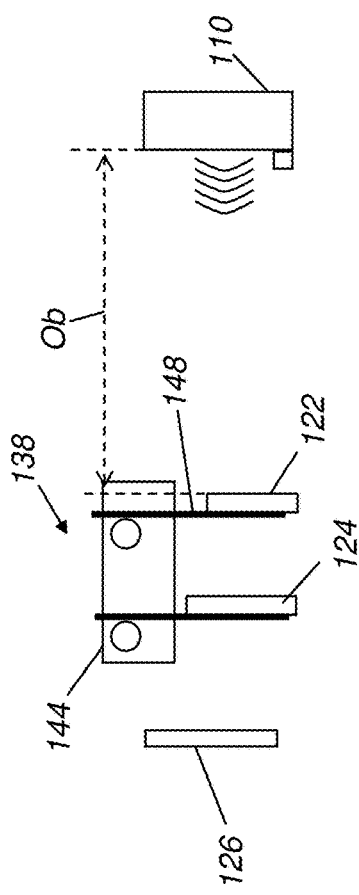
FIG. 12B shows the use of the detector positioning apparatus of FIG. 12A for CT imaging.
Figure 12C:
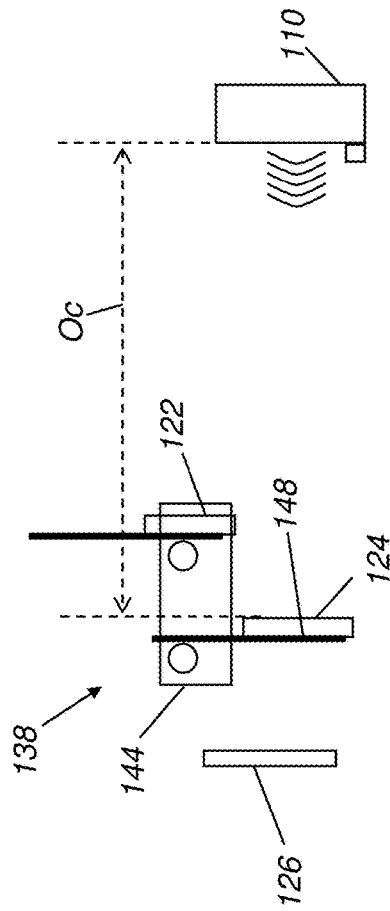
FIG. 12C shows the use of the detector positioning apparatus of FIG. 12A for panoramic imaging.

Referring to FIGS. 12A-12D, there is shown another alternate embodiment for positioning, supporting, and moving the various CT, panoramic, and cephalometric detectors 122, 124, and 126. Here, each of detectors 122 and 124 are on separate movable platens 148. FIG. 12A is a side view that shows a two-position detector positioning apparatus 138 having an elevator apparatus 144 for detector positioning. Here, elevator apparatus 144 is actuable to translate one or more of the detectors into or out of the exposure path in a direction that is orthogonal to the rotary arm. FIGS. 12B, 12C and 12D are each side views showing detector positioning for each of three detector types. FIG. 12B shows a side view with detector positioning apparatus 138 supporting detectors in a first position for CT imaging. Here, CT detector 122 is properly positioned unobstructed with respect to, and in the direct path of x-ray source 110 along the exposure path at distance Ob. FIG. 12C shows a side view with elevator assembly 144 of detector positioning apparatus 138 actuated to lift CT detector 122 out of the exposure radiation path to allow panoramic imaging. Here, panoramic detector 124 is positioned along the exposure path at distance Oc, unobstructed with respect to, and in the direct path of x-ray source 110. FIG. 12D shows a side view with elevator assembly 144 of detector positioning apparatus 138 actuated to lift panoramic detector 124 up and out of the exposure radiation path to allow cephalometric imaging. Both detectors 122 and 124 are translated by elevator 144, out of the path of exposure radiation between x-ray source 110 and cephalometric detector 126, so that cephalometric detector 126 is unobstructed with respect to, and in the direct path of x-ray source 110 on the exposure path at distance Od.

Figure 12E:
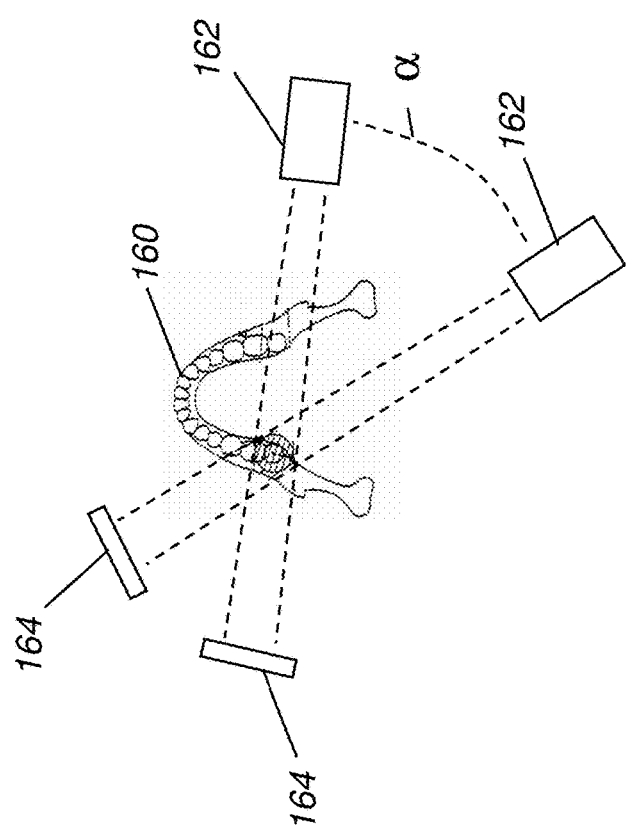
FIG. 12E shows a scan pattern used for partial CT imaging according to an embodiment of the present invention.

Embodiments of the present invention also use the photon-counting detector in partial CT scanning mode. Unlike full CT scanning, which can expose the patient to considerable amounts of radiation for obtaining volume image content, partial CT scanning uses a cone beam of reduced size and scans over a small range of angles to provide the volume data. Relative to the imaging apparatus used, partial CT imaging restricts the generated radiation from portions of the anatomy that are outside of the image area. In this way, partial CT is a more localized imaging mode, well suited to imaging a single tooth or group of adjacent teeth or other adjacent structures. Referring to FIG. 12E, there is shown part of a scan pattern for partial CT scanning, with a source 162 directing a narrowed cone beam of radiation to a photon-counting detector 164 through a portion of an arch 160.

Rotation for partial CT imaging is typically over a small range of angles, such as that shown as angle $\alpha$ in FIG. 12E. Angular rotation of as little as 5 degrees can be used for partial CT image acquisition. Other modifications to standard CT imaging include the use of cone beam radiation, typically modulated by providing the beam through a slit or narrowed collimator path, for example, instead of conventional fan beam radiation. Radiation can be continuously provided throughout the scan or pulsed, sensed at discrete angular intervals. The images acquired at different angles during the partial CT imaging sequence generally cover only a small area with this imaging modality. Rotation about a central axis, as shown in FIG. 12E, simplifies image processing and reconstruction.

According to an embodiment of the present invention, a slit or other mechanism is used to narrow the cone beam dimensions appropriately for partial CT scanning. The length of the slit corresponds to the length dimension of the corresponding detector 164; the overall shape of the directed beam of radiation is designed to be compatible with the aspect ratio of the photon-counting detector. Synchronous movement of detector 164 and source 162 thus allow volume image data to be acquired over a reduced range of angles using this imaging mode.

For partial CT imaging, a series of x-ray projection images is produced. Images that have been generated using the conical projection beam are stored and processed to obtain volume image data. Projection processing and methods used for 3 D volume image reconstruction are well known to those skilled in the optical imaging arts.

Each of the embodiments shown in FIGS. 10A-12D allows a measure of automation for setting up the proper detector in each position and for determining when the detector is suitably positioned so that imaging can proceed. For example, operator commands entered at an operator console (not shown) can be used to set up a second imaging type after a first image is obtained. Optionally, operator controls on rotary arm 140 can allow the imaging configuration to be shifted from one imaging type to another. Manual positioning may also be used, or some combination of manual and automated actuation for achieving each configuration. Different types of imaging sensors can be raised from or lowered into the path of incident radiation for various imaging types, for example. A movable carriage or other device can be used to switch the appropriate detectors into place as needed and to move unwanted detectors out of the path of radiation. When moved out of the imaging path, the imaging sensors may be shielded from exposure to radiation or to dirt.

According to an embodiment of the present invention, the same sensor is used for multiple types of imaging. Sensor response is treated differently for each imaging type. This can include windowing and other features that control how the exposure data is acquired for each imaging type. That is, the ranges of pixels that are read for each imaging type can be different.

Collimation can be used to control scanning of the exposure onto the detector. A slit, for example, can be formed and used for directing the radiation only along the slit, as the slit is scanned with respect to the sensor surface. Still other types of windowing may be used, including those that use the collimator or digital windowing algorithms that select the size of the area of the imaging sensor from which data is to be acquired. Image enlargement ratios can be adjusted according to the type of image data that is being obtained.

Offset detector geometry can be advantageous in some applications like CT imaging. The rectangular or roughly square shaped sensor is oriented in such a manner that the longitudinal axis extending from the generator to the sensor and passing through the rotation axis is perpendicular to the active surface of the sensor, the center of the sensor being offset transversely relative to the projection of the axis onto the active surface of the sensor. With photon-counting sensors, for example, a sensor offset or eccentricity can help to provide additional depth information for the scanned subject. For example, thanks to such an offset arrangement, on moving the ensemble source and photon counting sensor around the object in a full turn, a greater lateral extend of the object is captured. According to an embodiment of the present invention, the central axis of the radiation beam does not intersect the rotation axis.

Still other types of adjustment that are possible according to embodiments of the present invention include adjustment of a collimator 104, positioned in front of X-ray source 110 as shown in FIG. 9. The Field of View (FOV) of the imaging apparatus can be adjusted by changing the relative positions of the x-ray source and sensor as well as by making appropriate changes to tube voltage and current, as well as by collimator 104 adjustment.

The size of the FOV can be switched in a number of ways. According to one embodiment of the present invention, an operator interface on a control monitor allows selection of an FOV size. This selection then changes appropriate X-ray conditions (such as tube voltage and tube current, for example) according to the specified FOV size. A motor coupled with the collimator can also be adjusted to change the amount of light that is obtained by the imaging sensor or camera. As the FOV size is reduced with the same X-ray conditions, the light amount output to the imaging sensor decreases; proper collimator adjustment can help to remedy this problem.

As one example, the FOV can be changed between imaging of the whole jaw and imaging of a tooth ridge and nearby bones of one tooth. Here, the FOV size of X-rays is initially set for the whole jaw, a tomographic image is acquired of the whole jaw. Then, following adjustment of the FOV, a tomogram of one tooth is obtained and displayed. In this manner, when the whole jaw and one tooth are sequentially imaged, the resolution does not deteriorate, so that an image usable for assessment and diagnosis can be obtained. According to an alternate embodiment of the present invention, the FOV is adjusted automatically following operator selection of an imaging mode.

Rotation Axis Positioning Relative to the Patient and Imaging Apparatus

A number of different apparatus and methods can be used for positioning the patient relative to the axis of rotation of the x-ray apparatus. A chair or other device can be used to support the patient in position, so that the rotation axis can be adjusted accordingly. Various types of ear rods, head straps and supports, chin rests, bit blocks, and other devices can be used to position the head of the patient and to restrict patient movement. The various devices that are used can be employed in any of a number of combinations for constraining head movement and providing a reference for axis positioning.

According to an embodiment of the present invention, one or more light beams are used to indicate positions of the patient anatomy. The light beams can be sensed by one or more electronic sensors. According to an alternate embodiment of the present invention, light beams for horizontal and vertical alignment are directed toward the face and head of the patient and used as reference marks to guide head positioning. In the schematic view of FIG. 9, a light source 114 is used to provide this function, providing registration marks that enable the patient to be appropriately positioned for the type of imaging that is being performed. This can include, for example, reference positioning of the Frankfort plane, or other anatomical guideline. The use of guide beams in this way can provide information needed for automatic centering or adjustment of the rotation axis relative to the subject patient. For example, a vertical beam can correspond to a center (e.g., prescribed position, arc or boundary) of a region selected for imaging. A supporting display can be used in conjunction with an axis positioning system, enabling the practitioner to verify that the rotation axis is suitable for the anatomy that is being imaged.

The depth of the region around a selected scan curve that is in effectively sharp focus is known as the "focal layer thickness" or "focal trough." For dental imaging, where the panoramic view can be a perspective view of the dental arch with detail in the vertical and circumferential directions, or a portion thereof (e.g., as imaged from the inside or the outside), a view, but considerable focal trough depth in the radial direction, perpendicular to the plane of the image, is frequently desirable. Data from object features outside the effective focal trough are "smeared" out over different image pixels to such an extent that they contribute little to the final image. The wider the strip of sensors that is used to sum the image points, the more rapidly the data will cease to be related and become smeared as the distance from the selected image point at the center of the focal trough increases, and thus the smaller is the depth of focus of the final image.

Detection of the focal trough for panoramic imaging using the photon-counting detector can be performed in any of a number of ways. According to embodiments of the present invention, measurements of the dental arches are obtained to determine an axis for revolution of the X-ray source and sensor. Alternately, light beams are used to provide the best estimate for this axis, based on an estimate of the focal trough. The axis of rotation can also be adjusted during a panoramic imaging sequence, so that the movement of the axis of rotation correlates with the horseshoe-shaped pattern of the focal trough. In the example schematic of FIG. 9, for example, source translation apparatus 112 is actuated during the scan, moving the x-ray source 110 during rotation of rotary arm 140, effectively changing the axis of rotation in a continuous or discrete fashion as images are acquired. Default modeling of focal trough position and dimensions can alternately be used.

Focus depth for a region of interest can be calculated in a number of ways. According to an embodiment of the present invention, focus depth which is different in a region of interest can be distinguished from a focus depth corresponding to a predetermined panoramic image, wherein the focus depth for the region of interest is determined automatically, wherein the focus depth for the region of interest is determined by the processing device automatically by: calculating multiple layers using a laminographic reconstruction of the plural layers; calculating a measure of sharpness for each of the multiple calculated layers; and based on the calculated sharpness measure, choosing the sharpest layer from among multiple calculated layers for the region of interest to provide for and display a corrected layer for the region of interest defined for the panoramic image as a predetermined anatomical region defined by a predefined geometric path of the single source and detector, patient type, and a predetermined speed profile.

Focus depth for panoramic imaging and other imaging types can also be varied in a number of ways when using a photon-counting detector. According to an embodiment of the present invention, a user-identified region of interest (ROI) along a particular focal trough is defined. A variable focal pattern is used in the imaging scan, in order to obtain image data at different focal regions, indicative of tissue depth. For imaging a particular ROI, the corresponding image data can be obtained from the varied focal pattern used for acquiring the image content. The focus depth for an ROI for a panoramic or volume image can be automatically determined and can be different from the focus depth used for other images in the set of images obtained from the same patient during the same exam.

Figure 13:
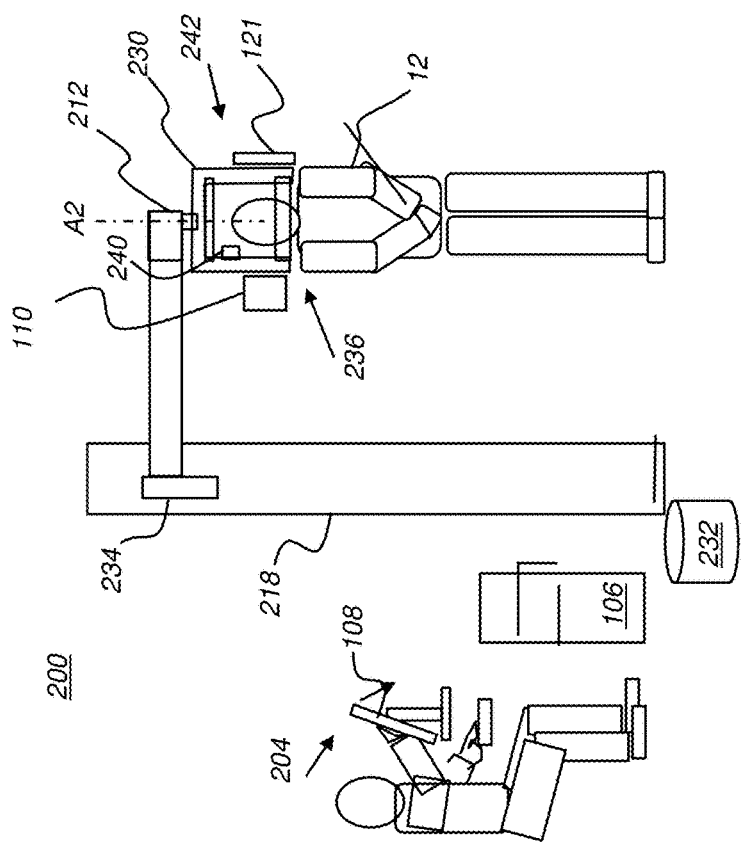
FIG. 13 is a schematic diagram showing an imaging apparatus for imaging portions of the patient's head using photon counting.

The schematic diagram of FIG. 13 shows an imaging apparatus 200 for radiographic imaging, such as panoramic imaging, in which a succession of two or more 2-D images is obtained and images of adjacent content are arranged to form a larger image, or for 3-D imaging, such as tomography, computed tomography volume imaging, or cone beam computed tomography (CBCT) imaging in dental, ENT, and related head imaging applications. A rotatable mount 230 is provided on a column 218, preferably adjustable in height to suit the size of patient 12. Mount 230 maintains x-ray source 110 and a radiation sensor 121 on opposite sides of the head of patient 12 and, optionally, rotates to orbit source 110 and sensor 121 in a scan pattern about the head. Mount 230 rotates about an axis A2 that corresponds to a central portion of the patient's head, so that its attached components orbit about the head. Sensor 121, a photon-counting sensor according to an embodiment of the present invention, is coupled to mount 230, opposite x-ray source 110 that emits a radiation pattern suitable for 2-D imaging, for tomosynthesis imaging, or for CT or CBCT volume imaging. Multiple sensors 121 can alternately be provided, as described previously, with the suitable sensor switched into place for each particular type of imaging. An optional head support 236, such as a chin rest or bite element, provides stabilization of the patient's head during image acquisition.

A computer 106 has an operator interface 204 and a display 108 for accepting operator commands and for display of volume images obtained by imaging apparatus 200. Computer 106 is in signal communication with sensor 121 for obtaining image data and provides signals for control of source 110 and, optionally, for control of a rotational actuator 212 for mount 230 components. One or more height sensors 234 is also sensed by computer 106 in order to obtain an initial height setting and to track relative vertical displacement of the sensor 121 relative to the patient's head during the helical scan. Computer 106 is also in signal communication with a memory 232 for storing image data. An optional alignment apparatus 240 is provided to assist in proper alignment of the patient's head for the imaging process. Alignment apparatus 240 includes a laser that provides one or more line references for head positioning according to an embodiment of the present invention. The alignment provided can be horizontal, vertical, or may specify position and angle, for example. Lines can display on the head or body of the patient. Alternately, light from the laser or other light source can be directed toward a photosensor element. In alternate embodiments, alignment apparatus 240 includes a visible light beam or other marker, or a mechanical or other positioning apparatus. Imaging apparatus 200 may also have the capability for panoramic or cephalometric imaging using x-ray source 110 and sensor 121 or other imaging sensor.

There can be a number of variable scan patterns according to the type of imaging that is required. Tomosynthesis, for example, typically uses a scan that revolves over an arc of less than 180 degrees about the patient. CBCT scanning may require a helical scan pattern with one or more revolutions about the patient's head. An optional adjustment mechanism 242 is provided for adjusting the source-to-image (SID) distance between the x-ray source 110 and sensor 121 to suit the scan pattern for different patients or different types of imaging.

An alternate scan pattern for extra-oral imaging shifts the position of the axis of rotation during the scan. This pattern, changing the focal trough progressively during the scan by adjusting the axis of rotation, allows improved imaging of different portions of the dental arch. According to an embodiment of the present invention, the location of the axis is changed with respect to two dimensions, that is, with respect to both x-and-y axes in the x-y plane that is normal to the axis of rotation. Changes in position can be along a line in the x-y plane, or along a curvilinear path, for example.

Multiple images can be obtained from a single exposure, using various techniques, with and without the thresholding capabilities of the photon-counting imaging detector.

One drawback of typical photon-counting image detectors is their relatively small size. Unlike a conventional digital radiography imaging panel that has an array with hundreds of elements in the height and width directions, the photon-counting sensor is typically of smaller size, with a width that may be fewer than 100 pixels in dimension. This problem can be addressed by tiling, an approach in which multiple image detectors are combined to cover a larger detection area. The use of polycrystalline materials, as opposed to conventional monocrystalline detector materials as noted earlier, can also help to provide larger detectors.

Figure 14:
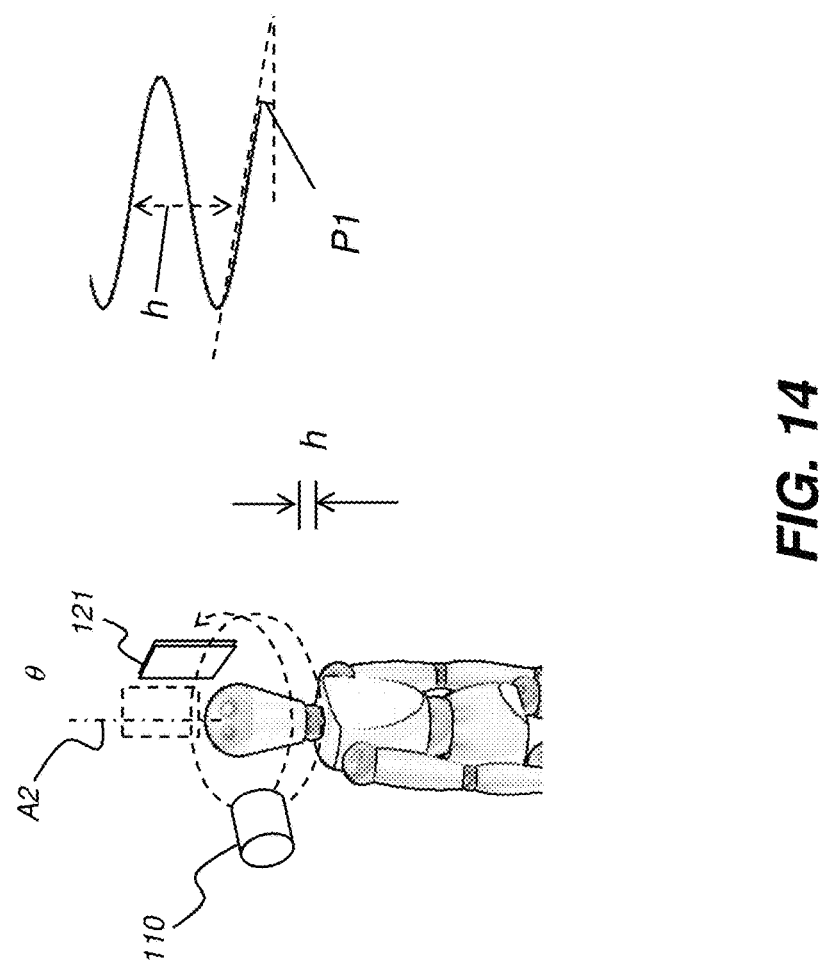
FIG. 14 is a schematic diagram that shows a portion of a helical scan for the digital sensor and radiation source.

Another solution for the size constraints of photon-counting image detectors adapts their scanning sequence to effectively increase the field of view. In practice, this size limitation requires a different scanning sequence from that used for conventional CBCT imaging. A helical scan can be used to acquire the needed image data for volume imaging. In operation, mount 230 rotates about the head of patient 12 multiple times, thereby scanning sensor 121 about patient 12 in a helical orbit, as is shown in FIG. 14. In FIG. 14, an adjacent imaging position is shown in dotted outline, with the angular distance exaggerated for clarity. According to an embodiment of the present invention, the vertical height h change of the helix during revolution of the source and detector, which can also be expressed in terms of the helical pitch angle P1, and angular change θ between successive image acquisitions, is adjustable.

Figures 15A, 15B:
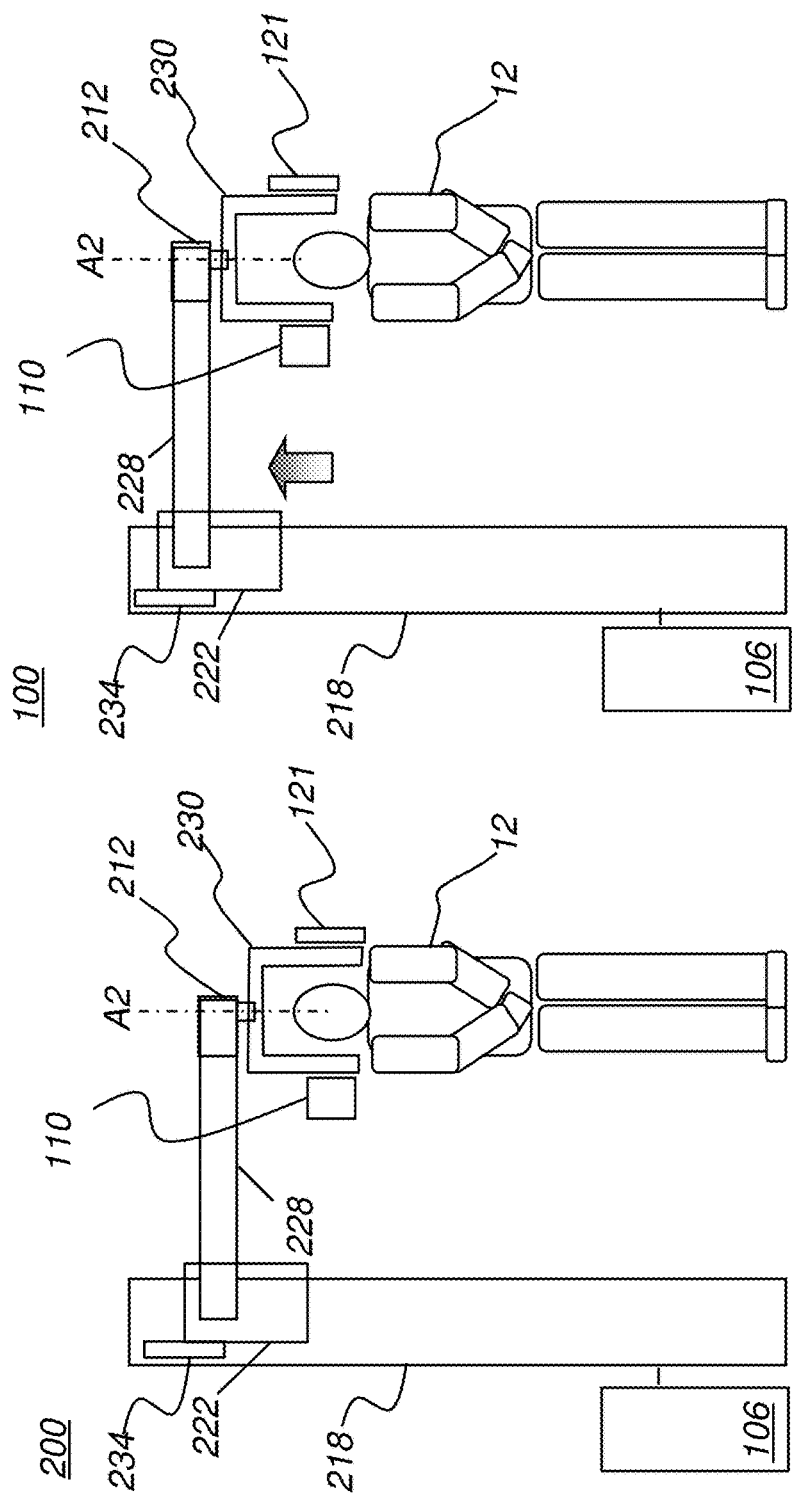
FIGS. 15A and 15B show the imaging apparatus that provides a helical scan by changing the elevation of a support arm during revolution about the patient.

The helical scan needed for CBCT imaging using a photon-counting sensor 121 can be provided following either of a number of scanning apparatus models. FIGS. 15A and 15B show a first approach to this problem, in which mount 230 that contains sensor 121 and source 110 is itself coupled to a movable travel arm 228 that is vertically translated during the scan, displaced by an actuator 212 during rotation of mount 230. This translation changes the relative vertical position of the imaging sensor and the radiation source to the patient's head during the helical scan.

Figures 17A, 17B:
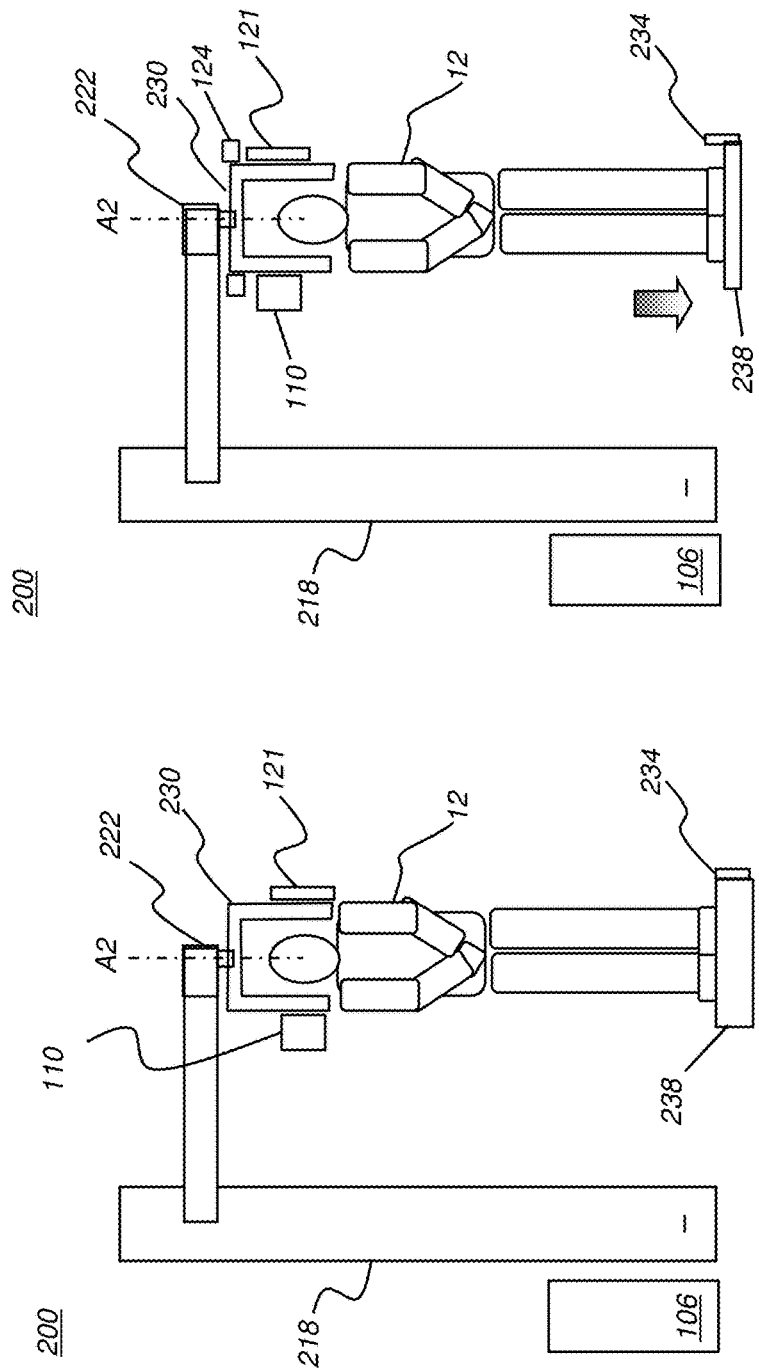
FIGS. 17A and 17B show the imaging apparatus that provides a helical scan by changing the elevation of the patient's head relative to the digital sensor and radiation source during revolution about the patient.

FIGS. 16A and 16B show a second approach to this problem, in which mount 230 itself has the same height, while source 110 and sensor 121 are vertically translated during the helical scan, thereby changing the relative vertical position of the imaging sensor and the radiation source to the patient's head during the helical scan. FIGS. 17A and 17B show a third approach to this problem, in which mount 230 itself has the same height, while a vertically adjustable platform 238 is used as an actuator to provide relative movement between the head of the patient and source 110 and sensor 121 for changing the relative vertical position of the imaging sensor and the radiation source to the patient's head during the helical scan.

As shown in FIGS. 15A-17B, one or more actuators 124 within mount 130, or other height adjustment devices provide this vertical translation function as source 110 and sensor 121 revolve about the patient's head. Computer 106 coordinates and tracks the vertical and rotational or angular movement and corresponding actuators needed for helical scanning. Sensor 134 provides feedback information on height with the FIG. 15A/B, FIG. 16A/B and FIG. 17A/B scan configurations.

Scanning can advance the position of the imaging sensor by less than a pixel between consecutive image frames.

Figure 18:
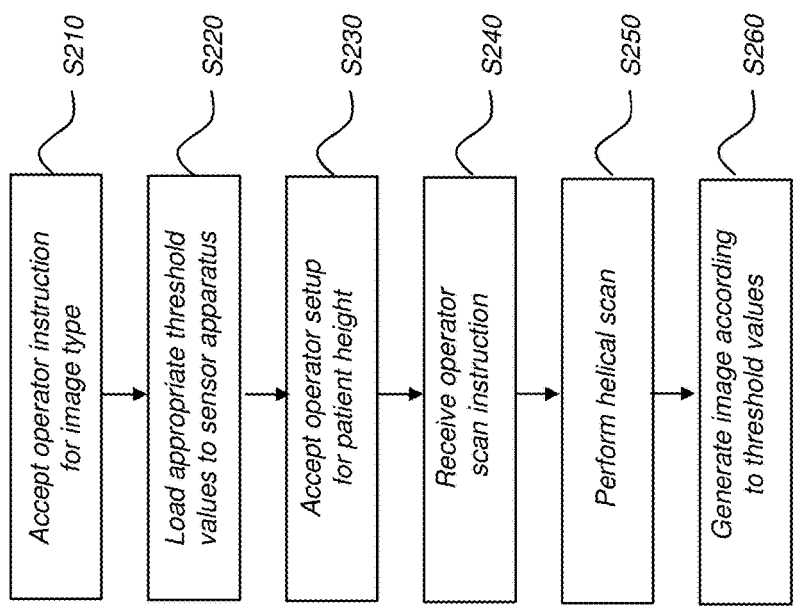
FIG. 18 is a logic flow diagram showing steps for image acquisition according to an embodiment of the present invention.

The logic flow diagram of FIG. 18 shows an operational sequence for CBCT scanning of the head using a photon-counting detector according to an embodiment of the present invention, for the imaging apparatus shown in FIGS. 14, 15A, 15B, 16A, 16B, 17A, and 17B. In an accept instruction step S210, the imaging apparatus accepts operator instructions related to the type of image to be obtained, which may include information on the types of tissue that are of particular interest. In a threshold setup step S220 an appropriate set of threshold values and other operational parameters is loaded to circuitry of sensor 121. An operator setup step S230 allows the operator to adjust mount 230 components to suit the height of the patient and size of the patient's head. This registers an initial height setting that provides information for subsequent helical scan execution. The operator can also use head support 236 and alignment apparatus 240 to adjust patient position. An instruction entry step S240 accepts the operator instruction to begin the scan sequence and to execute a scan and acquisition step S250. During step S250, multiple 2-D images are obtained at successive rotational and height positions for acquiring the CBCT scan data. An image generation step S260 then forms the 3-D volume image from the obtained 2-D images, using an image reconstruction algorithm, such as one of the filtered back-projection routines well known in the volume imaging arts. The resulting image is then displayed for viewing by the practitioner and the image data is stored in memory 232 (FIG. 13) or other memory circuitry that is accessible to computer 106.

According to an embodiment of the present invention, the tissue type of interest dictates the set of operational parameters that are most suitable for imaging a particular patient. By way of example, and not by way of limitation, Table 1 lists a set of parameters that are loaded when the operator elects to generate an image for tissue type A. Table 2 lists alternate example parameters for generating an image for tissue type B. As described earlier with respect to FIG. 14, the pitch of the helical scan pattern can be specified in terms of vertical translation or helical pitch angle P1. The helical pitch angle P1 can be varied from 0 degrees (that is, a slope of 0) to 40 degrees or more and is based on the relative size of the sensor 121 and the amount of overlap needed between successive images.

It can be appreciated that some modification of procedures listed and described with reference to FIG. 14 are similarly used for other types of imaging using imaging apparatus 100, with appropriate changes for the scan pattern and number of images obtained. For panoramic or tomosynthesis imaging, for example, a full scan is not needed. Only a partial scan is needed, with the scan orbit defined within a single plane, rather than helical as described for CBCT scanning.

TABLE 1

Operational Parameters for Tissue Type A

| Parameter | Setting |
|---|---|
| Radiation energy level | 30 kVp |
| Threshold values to sensor | +1.23 V |
|  | +1.41 V |
| Image acquisition interval | every 0.8 degrees |
| Vertical translation between images | 0.1 mm |

TABLE 2

Operational Parameters for Tissue Type B

| Parameter | Setting |
|---|---|
| Radiation energy level | 40 kVp |
| Threshold values to sensor | +1.02 V |
|  | +1.34 V |
| Image acquisition interval | every 0.9 degrees |
| Vertical translation between images | 0.12 mm |

As noted earlier, different types of materials have different photon energy "signatures", enabling the volume scan to detect two or more different materials in the imaged subject. This feature enables the same imaging apparatus to be employed for obtaining different information using the same scanning pattern. According to an embodiment of the present invention, different sets of threshold settings are provided, depending on the nature of the volume image that is desired. One set of threshold settings, for example, is optimized for obtaining information on teeth, while another set of threshold settings works best for imaging gum and underlying support structures. Still another set of threshold settings provides the best conditions for imaging of the throat, ear, or nasal passages, with corresponding elevation adjustments. As described with reference to FIG. 18, an appropriate set of threshold values is selected and loaded to the image acquisition circuitry of the imaging sensor according to the type of imaging that is to be performed and to the type of tissue that is of particular interest for a patient.

Embodiments of the present invention have been described for imaging various regions of the head and upper body of a patient using an extra-oral detector. The apparatus of the present invention can be used, for example, to obtain a full-mouth series (FMS) in dental practice. It should be noted that sensor 121 (FIGS. 13, 14) can combine photo-counting circuitry with other, conventional imaging components, such as with indirect detection or integrating imaging components described earlier with reference to FIGS. 4A-4D. Multiple sensors 121 can be coupled together to increase the area over which an image is obtained for each x-ray exposure. The photon-counting sensor 121 can be used to support different imaging modes, including CT or CBCT, panoramic, or cephalometeric imaging. CT and CBCT imaging modes obtain a volume image from multiple 2-dimensional (2-D) images. Panoramic and cephalometeric imaging are 2-dimensional imaging modes that may require scanning of sensor 121 in one or two directions within the same imaging plane during imaging in order to cover the full imaging area.

With the necessary adaptations to hardware and to the scanning patterns that are used, embodiments of imaging apparatus 200 (FIG. 13) are capable of a number of types of imaging, including 2-D imaging and panoramic imaging, tomosynthesis imaging, and volume imaging using computed tomography (CT) or cone-beam computed tomography (CBCT).

Tomosynthesis is an imaging mode that takes advantage of the capability of systems such as imaging apparatus 200 to localize focus over some fractional portion of an arc and to process the resulting image data in order to provide an image that provides some amount of depth information from a series of individual 2-D images obtained at different angles along the arc. Tomosynthesis thus provides a type of volume image with limited depth information, formed from a sequence of two-dimensional (2-D) images. Basic principles for dental tomosynthesis are known in the dental imaging arts and are described, for example, in U.S. Pat. No. 5,677,940.

One drawback of tomosynthesis techniques using photon-counting detectors relates to the discrepancy that can occur between the focus layer and the actual region of interest, such as the patient's teeth. Discrepancies can occur even when the focal layer (e.g., spline, locus of the rotation axis) is predefined for a given region along the dental arch or other structure. However, this disadvantage can be addressed or remedied by permitting the choice of a different, iteratively selected, or best focus layer that is different from the preset layer (e.g., for one or more portions of the preset layer) and by adapting the position of this best focus layer relative to the shape of the patient's dental arch. In processing, a shift of pixels within each image is performed, the amplitude of the shift chosen so that the position of the anatomical structure of interest is located, after shifting, at the same position on each image. After a pixel-to-pixel adding process of the plurality of acquired images, a final image is obtained in which the anatomical structure of interest is located in the focus layer and other structures are blurred (resulting in horizontal stripes, for example). By repeating the process with other shift amplitudes values, a plurality of focus layers can be obtained and the best one can be chosen for a region of interest. Among advantages of this technique are image quality, which is only slightly dependent upon the positioning of the patient.

It should be noted that extra-oral embodiments of the present invention can also provide an analog count, rather than using a digital counter arrangement. The accumulated analog charge, incremented once for each photon that is received, can be distinguished from conventional types of integrated radiation detection that provide a digital value according to the relative brightness of each pixel in the scintillator.

The scan curve can be altered by the user either interactively, such as during scanning and image acquisition, or following a particular scan sequence (e.g., at the image acquisition apparatus or by a viewer), such as with a panoramic image, for example.

Patient Positioning and Stabilization

Figure 19:
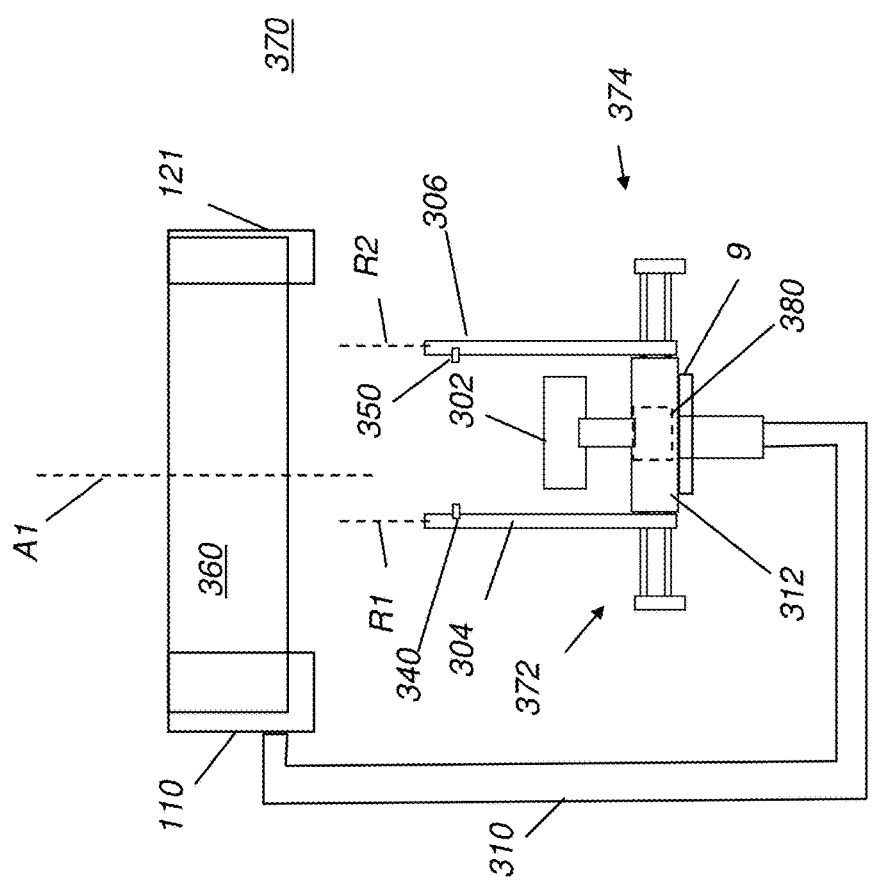
FIG. 19 is a schematic view showing components of a patient support apparatus.
Figure 20B:
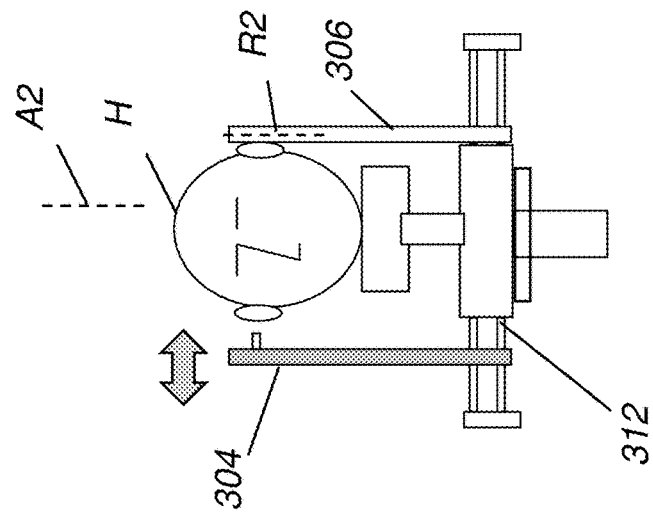
FIG. 20B shows alternate features of a head support for patient imaging.
Figure 20A:
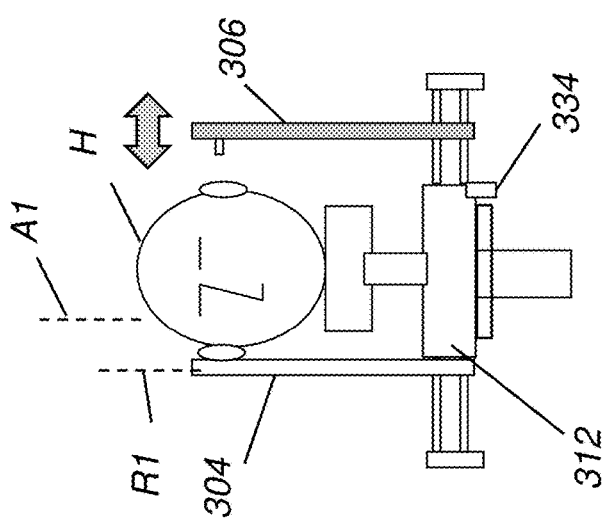
FIG. 20A shows features of a head support for patient imaging.

Patient support apparatus help to provide fixed reference positioning of the patient relative to the imaging system for obtaining a volume image when using a photon-counting sensor. The schematic views of FIGS. 19, 20A and 20B show features of a head support apparatus 370 at a rest position according to an embodiment of the present invention. Head support apparatus 370 mounts on a support structure 310 and has a main body, a base, and an optional chin rest 302. Temporal holding members 304 and 306 are positioned against the patient's head, each coupled to a transport apparatus, 372 and 374 respectively. Each holding member 304 and 306 has a respective reference position, shown as R1 and R2, respectively. Components of transport apparatus 372 and 374 include one or more shafts or other elements that extend outward, one from each side of a main body 312. Ear rods 340 and 350 are provided for seating within outer portions of the patients' ear cavity. In the rest position shown in FIG. 19, the distance between both ear rods 340 and 450 at the rest position is significantly smaller than the size of a patient's head. A rotatable gantry 360, also mounted on support structure 310, holds x-ray source 110 and sensor 121 for detecting x-rays and forming an image. Supporting structure 310 is representative in FIG. 19 and can take any number of forms for a standing or seated patient. Not shown are other conventional support components of the x-ray imaging apparatus, such as rotation mechanism for gantry 360 rotation, for example. A mouthpiece or bite structure could also be provided to help in further stabilizing the patient's head or in adjusting the head angle. As described in more detail subsequently, the position of axis of rotation A1 could vary, depending on whether reference position R1 or reference position R2 is fixed.

An extension locking mechanism 380 constrains movement of either of temporal holding members 304 and 306 at a time. As shown in FIG. 20A, when holding member 306 is moved outward from main body 312, holding member 304 is locked in its reference position R1. Similarly, as shown in FIG. 20B, when holding member 304 is moved outward from main body 312, holding member 306 is locked in its reference position R2. In this way, only one of holding members 304 or 306 can be moved outward at one time. At any one time, either holding member 304 is at reference position R1 or holding member 306 is at reference position R2. This allows alternative references for supporting patient head H in position relative to an axis of rotation A1 or A2 for gantry rotation of the x-ray source and sensor during imaging.

In one embodiment of the present invention, the axis of rotation can be set to either of two positions, shown as A1 and A2 in FIGS. 20A and 20B, allowing repositioning of the imaging gantry for imaging structures of the left or right ear when rotating along different axes, for example. Adjustment to position for axis A1 or A2 can be a mechanical adjustment made by an operator or may be automatically performed by control logic that operates the volume imaging apparatus. An optional sensor 334, as shown in FIG. 20A, enables control logic for the volume imaging apparatus to determine whether or not holding member 304 or 306 has been adjusted, so that proper axis selection can be enabled. Holding members 304 and 306 support corresponding ear rods 340 and 350 respectively. The vertical position of the chin support relative to the main body is adjustable and relative to the ears of the patient. When properly positioned using head support apparatus 370, the patient can be held on three non planar points: at the chin and at two ears, so that the patient's head is stabilized and does not move during imaging. Ears of the patient are in a well-defined position relative to the gantry and its related imaging components. It should be noted that the patient's head position can be different based on which holding member 304 or 306 is adjusted.

Figure 21:
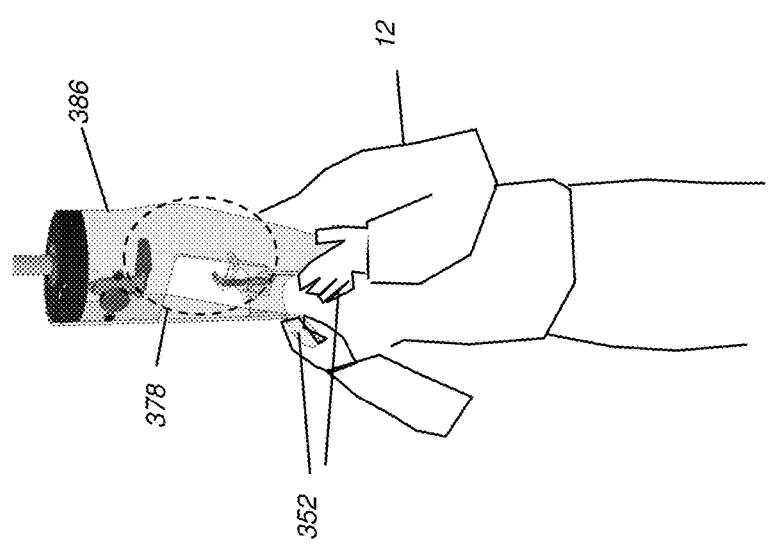
FIG. 21 shows use of a mask used for head and chin support during a volume imaging session.
Figure 22:
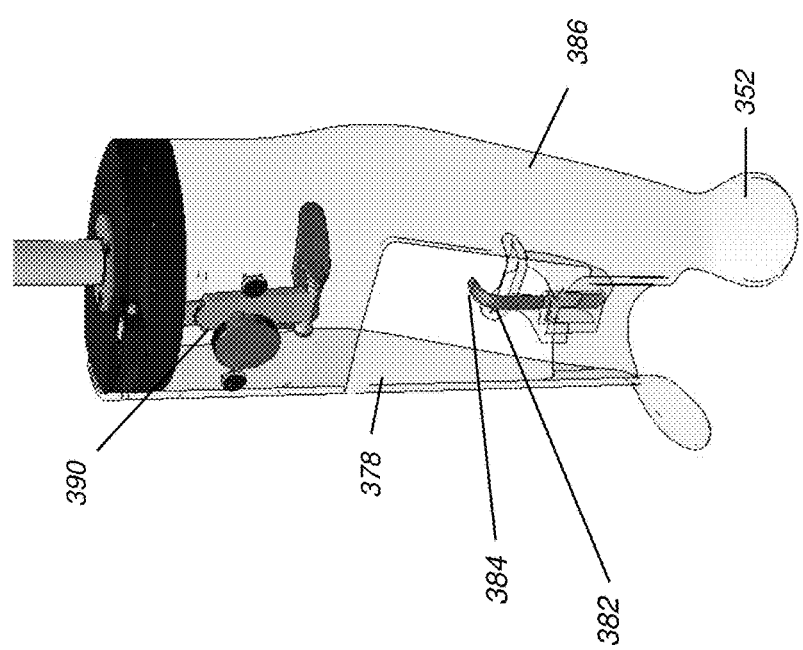
FIG. 22 shows components of a mask used for head and chin support during a volume imaging session.

As another alternative for patient support, a mask can be used, as shown in perspective views of FIGS. 21 and 22. Mask 386, as shown in FIG. 21, has handles 352 that allow the patient to grasp mask 386 for support and a window 378 for improved patient visibility. FIG. 22 shows components for supporting the head of the patient in position on mask 386. A chin rest 382 and bite support 384 are provided. Window 378 allows the patient to breathe more comfortably and allows better visibility for the patient and practitioner during setup. Mask 386 can be fully or partially transparent for even better visibility. Certain exemplary embodiments of patient supports can further provide positioning guidelines or marks (e.g., horizontal, vertical, alignment, spatial relationships) to assist an operator. An adjustable headrest 390 is also provided.

Control Functions

Various control functions are provided that allow setting of parameters and, where available, selecting one of multiple imaging types. Thus, for example, an operator can select image scanning and acquisition for CT, tomographic, 2-D, or panoramic imaging mode. In an alternate embodiment, the operator can specify an appropriate axis of rotation. These selections can be made on interface 204 (FIG. 13) or on some other control console, for example. Execution of operator instructions then causes the imaging apparatus to configure its arrangement of sensors for different imaging modes as well as to configure other aspects of system operation, such as collimator settings, voltage threshold levels, focus distance, and other parameters.

Image Processing and Reconstruction

For depth imaging when obtaining CT, panoramic, or other images, a set of images with multiple 2-D images is first obtained and stored. Images within the obtained set of images differ from each other according to the angle of imaging relative to the patient. In addition, images within the set acquired for a patient can also differ in radiation energy levels used, threshold energy levels detected, collimator positions and settings, region of the detector over which data is obtained, focus distance, and other characteristics.

A number of options are available for reconstruction of a volume image from individually obtained 2-D images when using a photon-counting image data sensor. Conventional methods for volume image reconstruction include the Feldkamp-Davis-Kreiss (FDK) method, an analytical reconstruction method that uses filtered back-projection to construct a 3-D image from individual 2-D slices. An alternate method, particularly useful where a limited number of 2-D image projections are available, is Algebraic Reconstruction Technique (ART) that iteratively solves a system of linear equations whose unknowns are corresponding image data values.

The focal trough of a panoramic image can be defined by parameters such as the trajectory of the axis of rotation during the scan. Then, a panoramic image can be reconstructed along a predetermined layer. Using the shift and add technique, a plurality of panoramic images can be reconstructed, on the basis of the same set of scan data (e.g., using a plurality of values of the shift). A panoramic image can also contain parts that are constructed using various shift and add values, then having various focal troughs. Such a construction can provide a good sharpness of the whole image or portions thereof, independent of the shape of the dental arch.

According to an embodiment of the present invention, reconstruction of the image data at different focal troughs can be performed using the data from a single scan. To obtain the image data during the scan, the focal trough can be continuously changed during the scan by adjusting the axis of rotation. Alternately, the focal trough can be switched during the scan in order to obtain image data from different portions of the dental arch. Switching of the focal trough can be performed, for example, by changing the position of the axis of rotation as well as by changing the effective focal position of the imaging apparatus.

Embodiments of the present invention provide a real time storage and retrieval of the collected and irradiated frames with a short time, such as with a delay of not more than one second. The reconstruction algorithm can reconstruct a panoramic layer or other depth image content from the stored and retrieved irradiated frames and display a panoramic layer or other feature in no later than 10 seconds from the end of an exposure series.

A shift-and-add algorithm, known in the art, can be used for image reconstruction. For this type of processing, the position of the current frame is recorded as a coordinate in the final image. This coordinate is then used to calculate an amount of shift required in a shift-and-add algorithm for reconstructing the final image. Sub-pixel shifting is accomplished by adding the pixels in a frame to two locations in the final image multiplied by suitable weighting factors. If the target position is x (non-integer or integer) and the position is increasing in a positive direction, then the pixel value is added to positions floor(x) and ceil(x) where floor (x) refers to the largest integer smaller than x and ceil(x) refers to the smallest integer larger than x. The respective weighting coefficients $w_{left}$ and $w_{right}$ are x-floor(x) and ceil(x)-x. The weighting factors $w_{left}$ and $w_{right}$ can be global to a single frame or can vary from pixel to pixel to compensate for any time delays between individual pixels.

This is mathematically equivalent to interpolating the frames and final image linearly in the horizontal direction, shifting the frame pixels in the horizontal direction by an integer amount and then down-sampling the frames and the final image to the original size. The sub-pixel shifting can also be implemented using any other interpolation method, for example with bi-linear, bi-cubic or spline interpolation.

An algorithm is provided which auto-focuses a panoramic layer and automatically calculates the layer-of-best-focus for dental panoramic imaging. The algorithm uses multiple image frames to compose a panoramic image of a layer of the object under observation, the image having a focus depth which is different in at least some part of the panoramic image from the focus depth corresponding to a predetermined panoramic image. In a first step, frame data is used to reset the change in velocity Δv of movement in the image plane compared to the change in original velocity .$Δv_{orig}$. In a second step, the user specifies a region of interest. In a third step, the region of interest is reconstructed at the original speed $V_{orig}$ plus the change in velocity, Δv. In a fourth step, the sharpness measure $S_{(n)}$ (sharpness measure S, which can either be a measure of contrast, roughness or some other measure of the image sharpness) and sharpness difference. ΔS is calculated as being equal to $S_{(n)}$ minus $S_{(n-1)}$SM ($V_{orig}$+Δv). In a fifth step, if ΔS is less than a particular limit, then the region of interest is displayed; otherwise, calculation uses a different step delta velocity Δv and returns to the third step and continues. The algorithm can be applied globally to the whole final image or locally to a given region-of-interest. Therefore the dentist is able to observe an initial panoramic image and then select a region (portion) of the image where blurring may be evident, in which case, the algorithm maximizes sharpness S of the selected part of the image. The result is a complete image with all parts well in focus.

Methods such as spine compensation can be used for providing images of improved quality for assessment of dental structures. Subtraction of blurred image content is used to provide this compensation, according to an embodiment of the present invention.

For the various embodiments shown, signal communication between components can use wired or wireless signal channels. The use of wireless communication can be advantaged, for example, for receiving signals from sensor devices that are difficult to maintain connection to. Wireless communication can also be used between sensor 121 and the image processor that obtains image data. Referring to FIGS. 15A and 15B, for example, sensor 121 communicates the acquired image data to computer 106 using wireless transmission according to an embodiment of the present invention. It should be noted that high transmission speeds are required for wireless transmission of image data, particularly for volume imaging applications that require that multiple 2-D images be obtained in order to reconstruct the 3-D image.

Consistent with an embodiment of the present invention, a computer executes a program with stored instructions that perform on image data accessed from an electronic memory. As can be appreciated by those skilled in the image processing arts, a computer program of an embodiment of the present invention can be utilized by a suitable, general-purpose computer system, such as a personal computer or workstation, as well as by a microprocessor or other dedicated processor or programmable logic device. However, many other types of computer systems can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape or other portable type of magnetic disk; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

It should be noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing processes and for recording entered values, such as seed points, or storing intermediate and final results of calculations and other processing. Computer-accessible memory can be volatile, non-volatile, or a hybrid combination of volatile and non-volatile types. Computer-accessible memory of various types is provided on different components throughout the system for storing or recording, processing, transferring, and displaying data, and for other functions.

The disclosed exemplary embodiments are considered in all respects to be illustrative and not restrictive. In addition, while a feature(s) of the invention can have been disclosed with respect to at least one of several implementations/embodiments, such feature can be combined with one or more other features of other implementations/embodiments as can be desired and/or advantageous for any given or identifiable function.

The invention claimed is:

1. An extra oral dental imaging apparatus for obtaining an image from a patient, the apparatus comprising:
   a radiation source;
   a digital imaging sensor that provides, for each of a plurality of image pixels, a first lowest energy value according to a count of received photons of ionizing radiation energy that exceed at least a first lowest energy value threshold;
   a mount that supports the radiation source in a spaced relationship relative to the first digital imaging sensor; with respect to an imaging area;
   a computer in signal communication with the first digital imaging sensor for acquiring one or more two-dimensional images from the digital imaging sensor; and
   a controller electrically coupled to the radiation source, the digital imaging sensor, the mount and the computer, the controller configured to operate the extra oral dental imaging apparatus in at least one imaging mode,
   wherein the digital imaging sensor further provides, for each of the plurality of image pixels, a second highest energy value obtained from a count of photons of ionizing radiation energy that exceed a second highest energy value threshold that is greater than the first lowest energy value threshold, wherein the digital imaging sensor further provides an upper threshold that is greater than the second highest energy value threshold, wherein the first lowest energy value is according to the count of received photons of ionizing radiation energy that both exceed the first lowest energy value threshold and are less than the upper threshold, and wherein the second highest energy value is according to the count of received photons of ionizing radiation energy that both exceed the second highest energy value threshold and are less than the upper threshold, and
   wherein an image is reconstructed using only the first lowest energy value and the second highest energy value for the plurality of image pixels.

2. The apparatus of claim 1, wherein the extra oral dental imaging apparatus is configured to operate in at least one imaging mode, wherein the at least one imaging mode comprises at least one of volume imaging, CT imaging, panoramic imaging, or cephalometric imaging.

3. The apparatus of claim 2, wherein the extra oral dental imaging apparatus is configured to selectably operate in both of the panoramic imaging mode and the cephalometric imaging mode, wherein the cephalometric imaging mode and the panoramic imaging mode are configured to share a single digital imaging sensor.

4. The apparatus of claim 3, wherein the extra oral dental imaging apparatus is configured to move the single digital imaging sensor to a first imaging position for use in the cephalometric imaging mode and to a second imaging position for use in the panoramic imaging mode, wherein the single digital imaging sensor is configured to move between the first imaging position and the second imaging position by operator action, responsive to an operator selection, or automatically based on imaging mode.

5. The apparatus of claim 2, wherein the dental apparatus is configured to selectably operate in both of the panoramic imaging mode and the CT imaging mode, wherein the CT imaging mode and the panoramic imaging mode are configured to share a single digital imaging sensor.

6. The apparatus of claim 5, wherein the single digital imaging sensor response is treated differently for each imaging mode.

7. The apparatus of claim 1, wherein a movable slit translates along the surface of the digital imaging sensor to provide a scan of image content.

8. The apparatus of claim 7, wherein the movable slit is provided by the collimator.

9. The apparatus of claim 1, wherein movement of the digital imaging sensor is used to determine the imaged area.

10. The imaging apparatus of claim 1, wherein windowing is provided by control of at least one selected portion of the sensor that are configured to be read out to generate an image.

11. The imaging apparatus of claim 1, wherein a photon counting sensor is provided as a retrofit to an existing panoramic imaging apparatus.

12. The imaging apparatus of claim 1, wherein the digital imaging sensor has an active area with a long dimension x and a short dimension y with x/y>1.5.

13. The imaging apparatus of claim 1, wherein a movable platen is used to mount a CT detector and a panoramic detector either adjacently or back to back.

14. The imaging apparatus of claim 13, wherein the movable platen is movable as a single element to provide rotational or other curvilinear translation for the CT detector and the panoramic detector.

15. The imaging apparatus of claim 1, wherein the mount is coupled to a rotational actuator that is energizable to revolve the digital imaging sensor and the radiation source in a scan pattern about a patient's head.

16. The apparatus of claim 15 further comprising one or more vertical actuators energizable for changing the relative vertical position of the digital imaging sensor and the radiation source to the patient's head, wherein the computer combines two or more images in the scan pattern to form a helical computed tomography image, and wherein the one or more vertical actuators translate the mount for changing the relative vertical position of the digital imaging sensor and the radiation source to the patient's head during imaging.

17. The imaging apparatus of claim 1 further comprising an alignment apparatus for providing alignment of a patient's head for obtaining the one or more two-dimensional images.

18. The imaging apparatus of claim 1 further comprising:
 a memory in communication with the computer for storing the one or more two-dimensional images; and
 at least one height sensor in communication with the computer.

19. The imaging apparatus of claim 1, wherein the radiation source is either continuous or pulsed.

20. The imaging apparatus of claim 19, wherein the radiation source is pulsed, and wherein the radiation source changes exposure levels from one exposure to the next.

* * * * *